United States Patent
Kwon et al.

(10) Patent No.: US 11,578,082 B2
(45) Date of Patent: Feb. 14, 2023

(54) COMPOUND AND FILM AND IR SENSOR AND COMBINATION SENSOR AND ELECTRONIC DEVICE

(71) Applicant: Samsung Electronics Co., Ltd., Suwon-si (KR)

(72) Inventors: Ohkyu Kwon, Seoul (KR); Rae Sung Kim, Hwaseong-si (KR); Dong-Seok Leem, Hwaseong-si (KR); Changki Kim, Suwon-si (KR); Insun Park, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 17/407,646

(22) Filed: Aug. 20, 2021

(65) Prior Publication Data

US 2022/0064182 A1     Mar. 3, 2022

(30) Foreign Application Priority Data

Aug. 31, 2020    (KR) ........................ 10-2020-0110629

(51) Int. Cl.
| | | |
|---|---|---|
| C07D 495/14 | (2006.01) | |
| C07D 409/04 | (2006.01) | |
| C07D 409/14 | (2006.01) | |
| C07D 495/04 | (2006.01) | |
| G01N 21/35 | (2014.01) | |
| H01L 51/44 | (2006.01) | |

(52) U.S. Cl.
CPC ......... *C07D 495/14* (2013.01); *C07D 409/04* (2013.01); *C07D 409/14* (2013.01); *C07D 495/04* (2013.01); *G01N 21/35* (2013.01); *H01L 51/441* (2013.01); *H01L 51/448* (2013.01)

(58) Field of Classification Search
None
See application file for complete search history.

(56) References Cited

U.S. PATENT DOCUMENTS

| 9,127,020 B2 | 9/2015 | Hildebrandt et al. |
|---|---|---|
| 2018/0259849 A1 | 9/2018 | Hirai et al. |

FOREIGN PATENT DOCUMENTS

| DE | 102013101712 A1 | 8/2014 |
|---|---|---|
| WO | WO-2016/124694 A1 | 8/2016 |

OTHER PUBLICATIONS

Extended European Search Report dated Jan. 26, 2022 for corresponding European Application No. 21192304.0.
Grassier Nico et al.: "Heteroquinoid Merocyanine Dyes with High Thermal Stability as Absorber Materials in Vacuum-Processed Organic Solar Cells", European Journal of Organic Chemistry, vol. 2019, No. 4, Jan. 31, 2019, pp. 845-851, XP055877360, DOI: 10.1002/ejoc.201801512, Retrieved from the Internet: URL: https://onlinelibrary.wiley.com/doi/full-XML/10.1002/ejoc.201801512>.
Begona Milian et al.: "Spectroscopic and Theoretical Study of Push-Pull Chromophores Containing Thiophene-Based Quinonoid Structures as Electron Spacers", Journal of Physical Chemistry Part B, vol. 107, No. 44, Nov. 1, 2003, pp. 12175-12183, XP055262328, DOI: 10.1021/jp0354651.
Holzmuller Felix et al.: "H-aggregated small molecular nanowires as near infrared absorbers for organic solar cells", Organic Electronics, vol. 45, Mar. 9, 2017, pp. 198-202, XP029985119, DOI: 10.1016/J.ORGEL.2017.03.009.
Inoue et al. "Donor-acceptor-substituted heteroquinoid chromophores as novel nonlinear optics", Synthetic Metals (1997), 84(1-3), 395-396.
Qian et al., "Simple and Efficient Near-Infrared Organic Chromophores for Light-Emitting Diodes with Single Electroluminescent Emission above 1000nm", Adv. Mater. 21, 111 (2009).
Yao et al. "Organic Bulk Heterojunction Infrared Photodiodes for Imaging Out to 1300 nm", ACS Appl. Electron. Mater., 1, 660 (2019).
Wu et al., "Elucidating the Detectivity Limits in Shortwave Infrared Organic Photodiodes", Adv. Funct. Mater. 28, 1800391 (2018).
Holzmuller et al., "H-aggregated small molecular nanowires as near infrared absorbers for organic solar cells", Org. Electron. 45, (2017) 198.

*Primary Examiner* — Samantha L Shterengarts
(74) *Attorney, Agent, or Firm* — Harness, Dickey & Pierce, P.L.C.

(57) ABSTRACT

A compound is represented by Chemical Formula 1. The compound may be included in, a film, an infrared sensor, a combination sensor, and/or an electronic device.

[Chemical Formula 1]

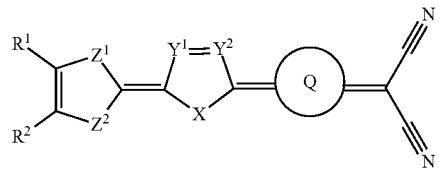

In Chemical Formula 1, X, $Y^1$, $Y^2$, $Z^1$, $Z^2$, Q, $R^1$, and $R^2$ are the same as described in the detailed description.

28 Claims, 13 Drawing Sheets

COMPOUND AND FILM AND IR SENSOR AND COMBINATION SENSOR AND ELECTRONIC DEVICE

CROSS-REFERENCE TO RELATED APPLICATION

This application claims priority to and the benefit under 35 U.S.C. § 119 of Korean Patent Application No. 10-2020-0110629 filed in the Korean Intellectual Property Office on Aug. 31, 2020, the entire contents of which are incorporated herein by reference.

BACKGROUND

1. Field

A compound, a film, an infrared sensor, a combination sensor, and an electronic device are disclosed.

2. Description of the Related Art

Imaging devices are used in digital cameras and camcorders, etc. to capture an image and to store the captured image as an electrical signal, and the imaging devices include a sensor separating the incident light into separate components defined by separate wavelength spectrums and converting each separate component to an electrical signal.

SUMMARY

Some example embodiments provide a compound that exhibits good light absorption properties and electrical properties in the infrared wavelength spectrum.

Some example embodiments provide a film including the compound.

Some example embodiments provide an infrared sensor including the compound. Such an infrared sensor may be configured to detect light in an infrared (IR) wavelength spectrum with improved sensitivity in a low illumination environment and/or may be configured to be used as a biometric device or a security device.

Some example embodiments provide a combination sensor including the compound or the infrared sensor.

Some example embodiments provide an electronic device including the compound, the infrared sensor, or the combination sensor.

According to some example embodiments, a compound represented by Chemical Formula 1 is provided.

[Chemical Formula 1]

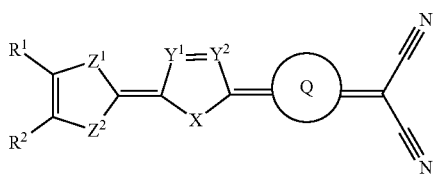

In Chemical Formula 1,
X is O, S, Se, Te, SO, $SO_2$, $NR^a$, $CR^bR^c$, or $SiR^dR^e$,
$Y^1$ and $Y^2$ are independently $CR^f$ or N,
one of $Z^1$ or $Z^2$ is S and another of $Z^1$ or $Z^2$ is O, S, Se, Te, or $NR^g$,
Q is a substituted or unsubstituted C3 to C30 quinoidal ring,
$R^1$ and $R^2$ are independently hydrogen, a substituted or unsubstituted C1 to C30 alkyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a substituted or unsubstituted silyl group, a halogen, or a combination thereof,
$R^a$ to $R^g$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof,
$R^1$ and $R^2$ are independently present or are linked to each other to form a ring,
$R^b$ and $R^c$ are independently present or are linked to each other to form a ring,
$R^d$ and $R^e$ are independently present or are linked to each other to form a ring, and
adjacent $R^f$'s are independently present or are linked to each other to form a ring.

Q in Chemical Formula 1 may include at least one substituted or unsubstituted 5-membered quinoidal ring, at least one substituted or unsubstituted 6-membered quinoidal ring, or a fused ring thereof.

Q in Chemical Formula 1 may be one of the groups listed in Group 1.

[Group 1]

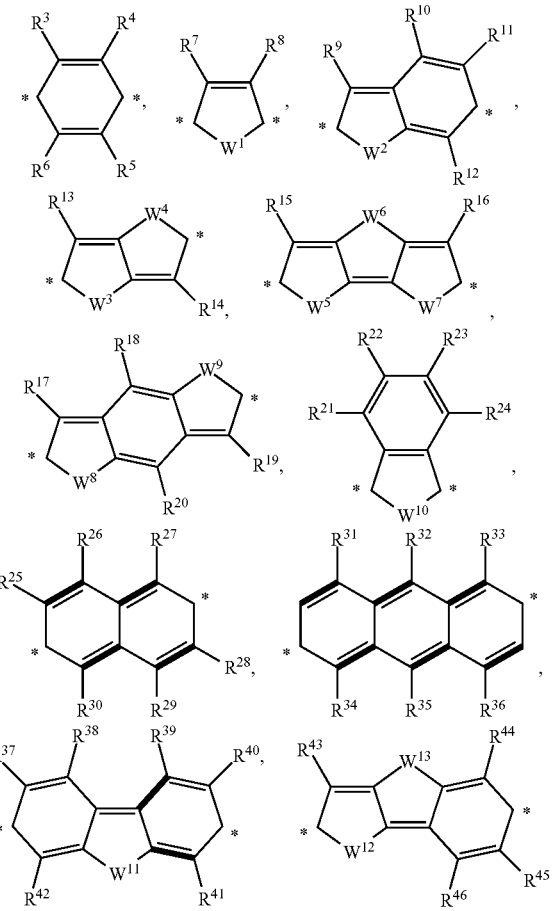

In Group 1,
$W^1$ is different from X and is S, Se, or Te,
$W^2$ to $W^{13}$ are independently S, Se, or Te, $R^3$ to $R^{46}$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof, $R^3$ to $R^{46}$ are independently present or adjacent two of $R^3$ to $R^{46}$ are linked to each other to provide a ring, and

* is a linking point with Chemical Formula 1.

X, $Z^1$, and $Z^2$ of Chemical Formula 1 may be each S.

The compound may be represented by one of Chemical Formulas 1A to 1I.

[Chemical Formula 1A]

[Chemical Formula 1B]

[Chemical Formula 1C]

[Chemical Formula 1D]

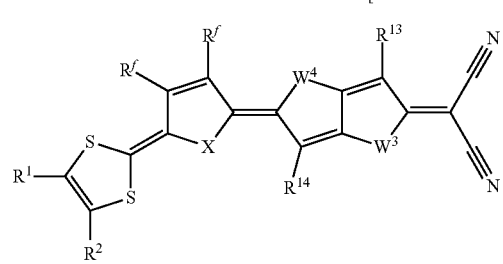

[Chemical Formula 1E]

[Chemical Formula 1F]

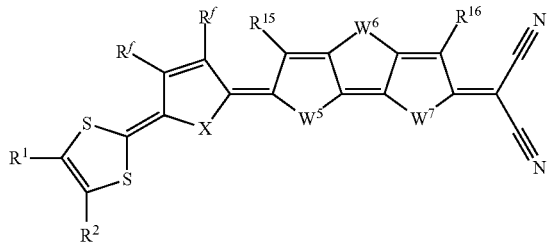

[Chemical Formula 1G]

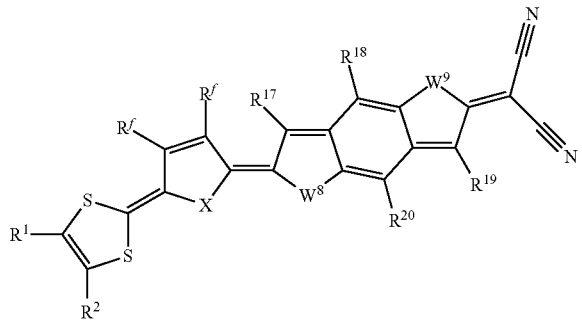

[Chemical Formula 1H]

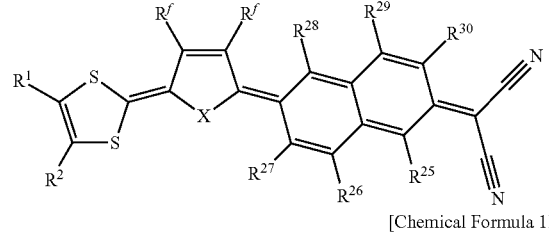

[Chemical Formula 1I]

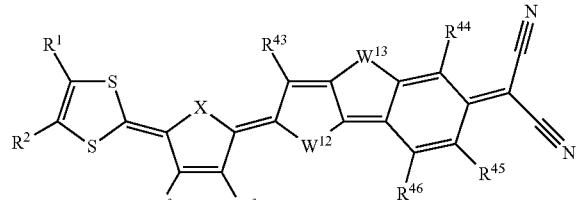

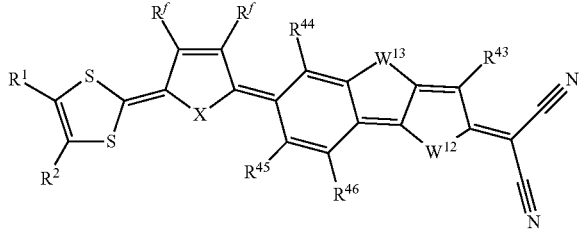

In Chemical Formula 1A to 1I,

X is O, S, Se, Te, SO, $SO_2$, $NR^a$, $CR^bR^c$, or $SiR^dR^e$, where $R^a$ to $R^e$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof, $W^2$ to $W^9$, $W^{12}$, and $W^{13}$ are independently S, Se, or Te, $R^1$ and $R^2$ are independently hydrogen, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a substituted or unsubstituted silyl group, a halogen, or a combination thereof, and $R^3$ to $R^6$, $R^9$ to $R^{20}$, $R^{25}$ to $R^{30}$, $R^{43}$ to $R^{46}$, and $R^f$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof.

The compound may be represented by one of Chemical Formulas 1A-1 to 1I-1.

[Chemical Formula 1A-1]

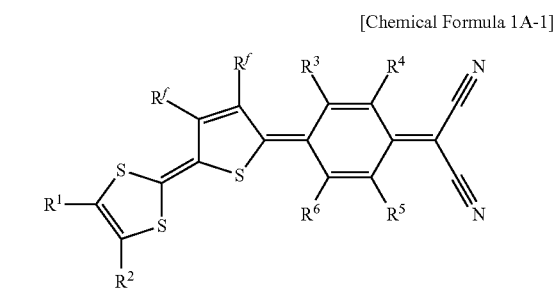

[Chemical Formula 1B-1]

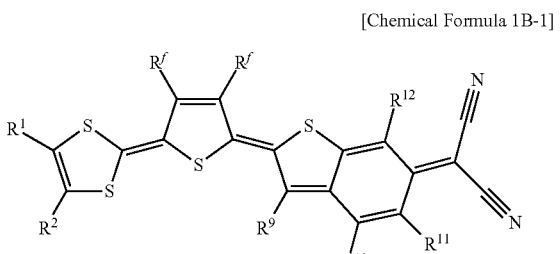

[Chemical Formula 1C-1]

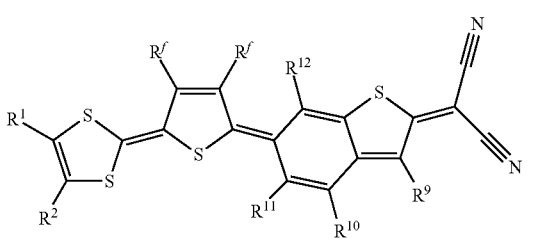

[Chemical Formula 1D-1]

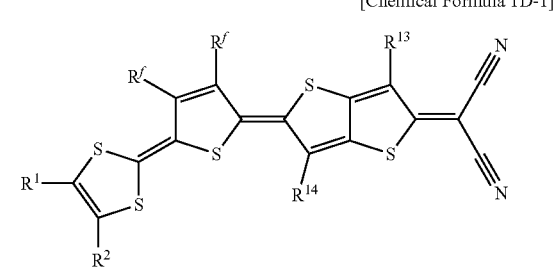

[Chemical Formula 1E-1]

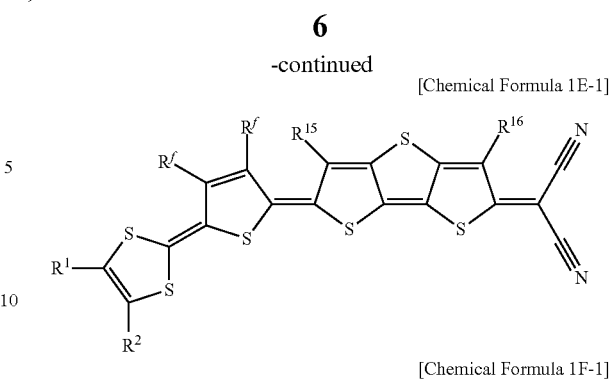

[Chemical Formula 1F-1]

[Chemical Formula 1G-1]

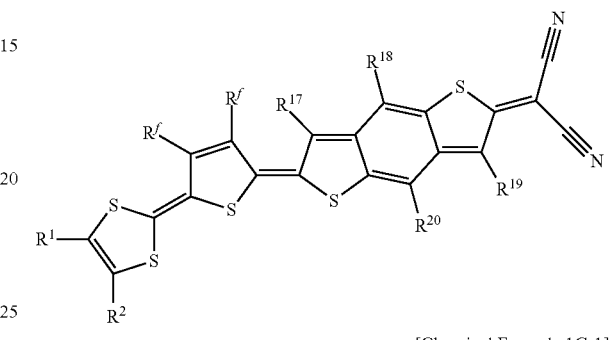

[Chemical Formula 1H-1]

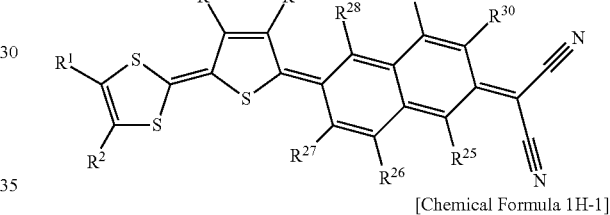

[Chemical Formula 1I-1]

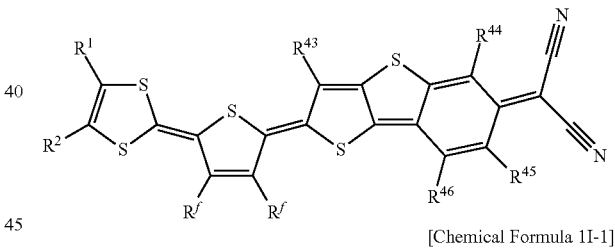

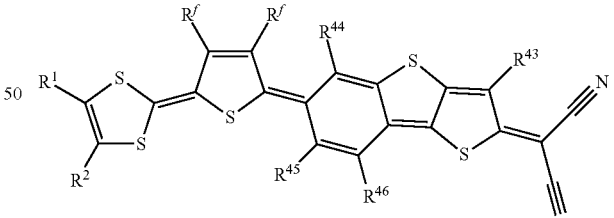

In Chemical Formulas 1A-1 to 1I-1, $R^1$ and $R^2$ are independently hydrogen, a substituted or unsubstituted C1 to C30 alkyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a substituted or unsubstituted silyl group, a halogen, or a combination thereof, and $R^3$ to $R^6$, $R^9$ to $R^{20}$, $R^{25}$ to $R^{30}$, $R^{43}$ to $R^{46}$, and $R^f$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof.

According to some example embodiments, a film including the compound is provided.

The film may have a peak absorption wavelength in a wavelength range of about 800 nm to about 3000 nm.

According to some example embodiments, an infrared sensor includes a first electrode and a second electrode facing each other, and an organic layer between the first electrode and the second electrode and including the compound represented by Chemical Formula 1.

A wavelength exhibiting a peak external quantum efficiency of the infrared sensor may belong to a wavelength range of about 800 nm to about 3000 nm, such that the infrared sensor exhibits a peak external quantum efficiency (EQE) with regard to incident light at a peak EQE wavelength that belongs to a wavelength range of about 800 nm to about 3000 nm.

The organic layer may include an infrared photoelectric conversion layer, the infrared photoelectric conversion layer may include the compound and a counter material forming a pn junction with the compound.

The infrared sensor may include an infrared photoelectric conversion layer, and an auxiliary layer that is at least one of between the first electrode and the infrared photoelectric conversion layer or between the second electrode and the infrared photoelectric conversion layer.

The infrared photoelectric conversion layer may include the compound, and the auxiliary layer may include ytterbium (Yb), calcium (Ca), potassium (K), barium (Ba), magnesium (Mg), lithium fluoride (LiF), or an alloy thereof.

The auxiliary layer may include the compound.

The infrared sensor may further include a semiconductor substrate.

According to some example embodiments, a combination sensor includes a first infrared sensor that is the infrared sensor and a second infrared sensor configured to detect incident light in a shorter wavelength spectrum or a longer wavelength spectrum than the first infrared sensor within an infrared wavelength spectrum, wherein the first infrared sensor and the second infrared sensor are stacked with each other in a depth direction that is perpendicular to an in-plane direction of the first infrared sensor.

According to some example embodiments, a combination sensor includes the infrared sensor and a visible light sensor configured to detect at least a portion of incident light in a visible light wavelength spectrum.

The combination sensor may further include a semiconductor substrate, and the infrared sensor may be arranged in parallel with the visible light sensor along an in-plane direction of the semiconductor substrate, or may be stacked with the visible light sensor along a depth direction of the semiconductor substrate.

The visible light sensor may include a blue sensor configured to sense light in a blue wavelength spectrum, a green sensor configured to sense light in a green wavelength spectrum, and a red sensor configured to sense light in a red wavelength spectrum, and each of the blue sensor, the green sensor, and the red sensor may be a photodiode integrated in a semiconductor substrate.

The visible light sensor may include a blue sensor configured to sense light in a blue wavelength spectrum, a green sensor configured to sense light in a green wavelength spectrum, and a red sensor configured to sense light in a red wavelength spectrum, wherein two of the blue sensor, the green sensor, or the red sensor may be photodiodes integrated in a semiconductor substrate, and the other of the blue sensor, the green sensor, or the red sensor may be a visible light photoelectric conversion device on the semiconductor substrate and stacked with the infrared sensor in a depth direction that is perpendicular to an in-plane direction of the infrared sensor.

The visible light sensor may include a blue sensor configured to sense light in a blue wavelength spectrum, a green sensor configured to sense light in a green wavelength spectrum, and a red sensor configured to sense light in a red wavelength spectrum, and each of the blue sensor, the green sensor, and the red sensor may be a visible light photoelectric conversion device stacked with the infrared sensor.

The infrared photoelectric conversion layer may include an intrinsic layer including the compound and the counter material in a volume ratio of about 1:9 to about 9:1.

The infrared photoelectric conversion layer may have a thickness of about 80 nm to about 300 nm.

The first infrared sensor may be configured to sense a portion of the incident light that includes at least a first wavelength in the infrared wavelength spectrum, the first wavelength being a peak absorption wavelength of the first infrared sensor. The second infrared sensor may be configured to sense another portion of the incident light that includes at least a second wavelength in the infrared wavelength spectrum, the second wavelength being a peak absorption wavelength of the second infrared sensor. A difference between the first wavelength and the second wavelength may be between about 70 nm and about 150 nm.

The film may have a thickness of about 1 nm to about 30 μm.

According to some example embodiments, an infrared sensor may include a first electrode and a second electrode facing each other, an infrared photoelectric conversion layer between the first electrode and the second electrode, and an auxiliary layer that is at least one of between the first electrode and the infrared photoelectric conversion layer, or between the second electrode and the infrared photoelectric conversion layer, wherein at least one of the infrared photoelectric conversion layer or the auxiliary layer includes the compound represented by Chemical Formula 1.

The compound may be one of Compound A, Compound B, or Compound C:

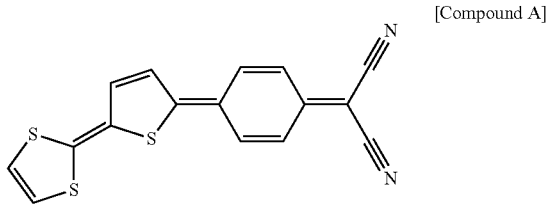

[Compound A]

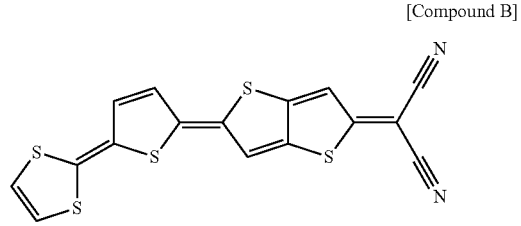

[Compound B]

-continued

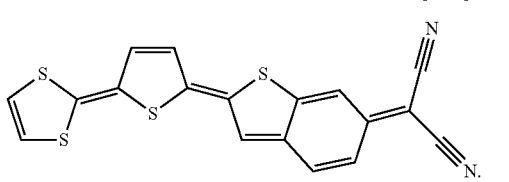
[Compound C]

The compound may exhibit a peak absorption wavelength in a wavelength spectrum of about 700 nm to about 1000 nm.

The infrared sensor may be configured to exhibit a peak external quantum efficiency (EQE) at a peak EQE wavelength of the infrared sensor, the peak EQE wavelength of the infrared sensor being between about 1000 nm and about 3000 nm.

According to some example embodiments, an electronic device including the compound, the film, the infrared sensor, or the combination sensor is provided.

The compound may exhibit good light absorption properties and electrical properties in the infrared region and thus may be effectively applied to a sensor.

DETAILED DESCRIPTION

Figure 1:
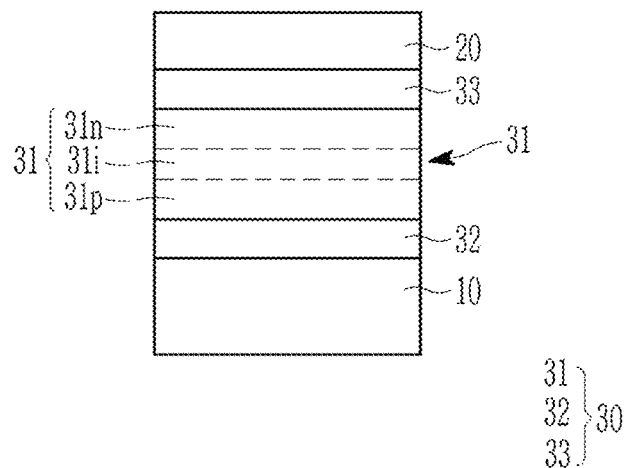
FIG. 1 is a cross-sectional view showing an example of an infrared sensor according to some example embodiments.

Hereinafter, example embodiments will be described in detail so that those of ordinary skill in the art can easily implement them. However, a structure that is actually applied may be implemented in various different forms, and is not limited to the example embodiments described herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present. It will further be understood that when an element is referred to as being "on" another element, it may be above or beneath or adjacent (e.g., horizontally adjacent) to the other element.

It will be understood that elements and/or properties thereof (e.g., structures, surfaces, directions, or the like), which may be referred to as being "perpendicular," "parallel," "coplanar," or the like with regard to other elements and/or properties thereof (e.g., structures, surfaces, directions, or the like) may be "perpendicular," "parallel," "coplanar," or the like or may be "substantially perpendicular," "substantially parallel," "substantially coplanar," respectively, with regard to the other elements and/or properties thereof.

Elements and/or properties thereof (e.g., structures, surfaces, directions, or the like) that are "substantially perpendicular" with regard to other elements and/or properties thereof will be understood to be "perpendicular" with regard to the other elements and/or properties thereof within manufacturing tolerances and/or material tolerances and/or have a deviation in magnitude and/or angle from "perpendicular," or the like with regard to the other elements and/or properties thereof that is equal to or less than 10% (e.g., a. tolerance of ±10%).

Elements and/or properties thereof (e.g., structures, surfaces, directions, or the like) that are "substantially parallel" with regard to other elements and/or properties thereof will be understood to be "parallel" with regard to the other elements and/or properties thereof within manufacturing tolerances and/or material tolerances and/or have a deviation in magnitude and/or angle from "parallel," or the like with regard to the other elements and/or properties thereof that is equal to or less than 10% (e.g., a. tolerance of ±10%).

Elements and/or properties thereof (e.g., structures, surfaces, directions, or the like) that are "substantially coplanar" with regard to other elements and/or properties thereof will be understood to be "coplanar" with regard to the other elements and/or properties thereof within manufacturing tolerances and/or material tolerances and/or have a deviation in magnitude and/or angle from "coplanar," or the like with regard to the other elements and/or properties thereof that is equal to or less than 10% (e.g., a. tolerance of ±10%).

It will be understood that elements and/or properties thereof may be recited herein as being "the same" or "equal" as other elements, and it will be further understood that elements and/or properties thereof recited herein as being "identical" to, "the same" as, or "equal" to other elements may be "identical" to, "the same" as, or "equal" to or "substantially identical" to, "substantially the same" as or "substantially equal" to the other elements and/or properties thereof. Elements and/or properties thereof that are "substantially identical" to, "substantially the same" as or "substantially equal" to other elements and/or properties thereof will be understood to include elements and/or properties thereof that are identical to, the same as, or equal to the other elements and/or properties thereof within manufacturing tolerances and/or material tolerances. Elements and/or properties thereof that are identical or substantially identical to and/or the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same and/or identical encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

As used herein, when a definition is not otherwise provided, "substituted" refers to replacement of hydrogen of a compound or a group by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a silyl group, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C30 alkylthio group, a C1 to C20 heteroalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when a definition is not otherwise provided, "hetero" refers to one including 1 to 4 heteroatoms selected from N, O, S, Se, Te, Si, and P.

As used herein, when a definition is not otherwise provided, "aromatic ring" refers to a functional group in which all atoms in the cyclic functional group have a p-orbital, wherein these p-orbitals are conjugated. For example, the aromatic ring may be a C6 to C30 aryl group or a C2 to C30 heteroaryl group.

As used herein, when a definition is not otherwise provided, "aryl group" refers to a group including at least one hydrocarbon aromatic moiety. All elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties may be fused directly or indirectly to provide a non-aromatic fused ring, for example a fluorenyl group. The aryl group may include a monocyclic, polycyclic or fused polycyclic (i.e., rings sharing adjacent pairs of carbon atoms) functional group.

As used herein, when a definition is not otherwise provided, "heterocycle" or "heterocyclic group" is a higher concept including "heteroaryl group", and may include at least one heteroatom selected from N, O, S, Se, Te, P, and Si instead of carbon (C) in the ring. When the heterocycle is a fused ring, the heterocycle may have at least one hetero atom, and each ring may have a hetero atom.

As used herein, when a definition is not otherwise provided, "ring" refers to an aromatic ring, non-aromatic ring, hetero aromatic ring, hetero non-aromatic ring, fused ring, and/or a combination thereof. The aromatic ring may be a C6 to C30 aryl group or a C2 to C30 heteroaryl group and the non-aromatic ring may be a C3 to C30 cycloalkyl group, a C3 to C30 cycloalkenyl group, a C3 to C30 cycloalkynyl group, a C3 to C30 heterocycloalkyl group, a C3 to C30 heterocycloalkenyl group, or a C3 to C30 heterocycloalkynyl group.

Hereinafter, a work function, a HOMO energy level, or a LUMO energy level is expressed as an absolute value from a vacuum level. In addition, when the work function, HOMO energy level, or LUMO energy level is referred to be deep, high, or large, it may have a large absolute value based on "0 eV" of the vacuum level while when the work function, HOMO energy level, or LUMO energy level is referred to be shallow, low, or small, it may have a small absolute value based on "0 eV" of the vacuum level.

Hereinafter, an energy bandgap refers to an absolute value of a difference between the HOMO energy level and LUMO energy level, the wide energy bandgap means that an absolute value of the difference between the HOMO energy level and LUMO energy level is large.

Hereinafter, the term 'metal' includes a metal and a semimetal.

Hereinafter, a compound according to some example embodiments is described. In some example embodiments, a composition may include the compound.

The compound according to some example embodiments may be a light absorbing material, and may be an infrared light absorbing material configured to absorb light in an infrared wavelength spectrum. The compound according to some example embodiments may be a light absorption semiconductor, or an infrared photoelectric conversion material configured to absorb light in an infrared wavelength spectrum and convert the absorbed light into an electrical signal.

The compound according to some example embodiments may be represented by Chemical Formula 1.

[Chemical Formula 1]

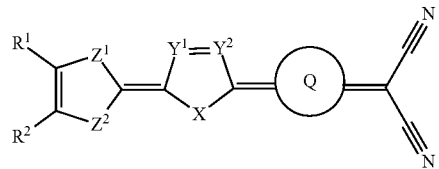

In Chemical Formula 1,
X is O, S, Se, Te, SO, SO$_2$, NR$^a$, CR$^b$R$^c$, or SiR$^d$R$^e$,
Y$^1$ and Y$^2$ are independently CR$^f$ or N,
one of Z$^1$ or Z$^2$ is S and the other of Z$^1$ or Z$^2$ is O, S, Se, Te, or NR$^g$,
Q is a substituted or unsubstituted C3 to C30 quinoidal ring,
R$^1$ and R$^2$ are independently hydrogen, a substituted or unsubstituted C1 to C30 alkyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a substituted or unsubstituted silyl group, a halogen, or a combination thereof, $R^a$ to $R^g$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof, $R^1$ and $R^2$ are independently present (e.g., are not linked to each other to provide a ring) or are linked to each other to provide (e.g., form) a ring, $R^b$ and $R^c$ are independently present or are linked to each other to provide a ring, $R^d$ and $R^e$ are independently present or are linked to each other to provide a ring, and adjacent $R^f$'s are independently present or are linked to each other to provide a ring.

The compound represented by Chemical Formula 1 has a chalcogen-containing heterocyclic group and malononitrile at both terminal ends and thus may form very large dipole moments due to strong electron-donating characteristics and electron-accepting characteristics and also, effectively adjust a length and planarity of molecule by two quinoidal rings between both terminal ends. Herein, a quinoidal ring is a ring structure derived from oxidation of an aromatic ring, a heteroaromatic ring, or a fused ring thereof. Accordingly, the compound may be effectively configured to absorb light in an infrared wavelength spectrum and exhibit satisfactory photoelectric conversion properties.

For example, X may be O, S, Se, Te, or $NR^a$, for example O, S, Se, or Te, for example S, Se, or Te, for example S or Se, for example S.

For example, $Y^1$ and $Y^2$ may each independently be $CR^f$, for example CH, respectively.

For example, one of $Z^1$ or $Z^2$ may be S and the other of $Z^1$ or $Z^2$ may be S, Se, or Te, for example one of $Z^1$ or $Z^2$ may be S and the other of $Z^1$ or $Z^2$ may be S or Se, and for example $Z^1$ and $Z^2$ may each independently be S.

For example, X, $Z^1$, and $Z^2$ may each independently be S or Se, and may be for example S.

For example, Q may include at least one substituted or unsubstituted 5-membered quinoidal ring, at least one substituted or unsubstituted 6-membered quinoidal ring, or a fused ring thereof. For example, Q may be one, two, or three substituted or unsubstituted 5-membered quinoidal rings; a fused ring of one, two, or three substituted or unsubstituted 5-membered quinoidal rings; one, two, or three substituted or unsubstituted 6-membered quinoidal rings; a fused ring of one, two, or three substituted or unsubstituted 6-membered quinoidal rings; a fused ring of one or two substituted or unsubstituted 5-membered quinoidal rings and one or two substituted or unsubstituted 6-membered quinoidal rings; or a combination thereof. However, when Q is a substituted or unsubstituted 5-membered quinoidal ring, Q may be different from an adjacent ring (5-membered quinoidal ring including X, $Y^1$, and $Y^2$).

For example, Q may be one of the groups listed in Group 1, but is not limited thereto.

[Group 1]

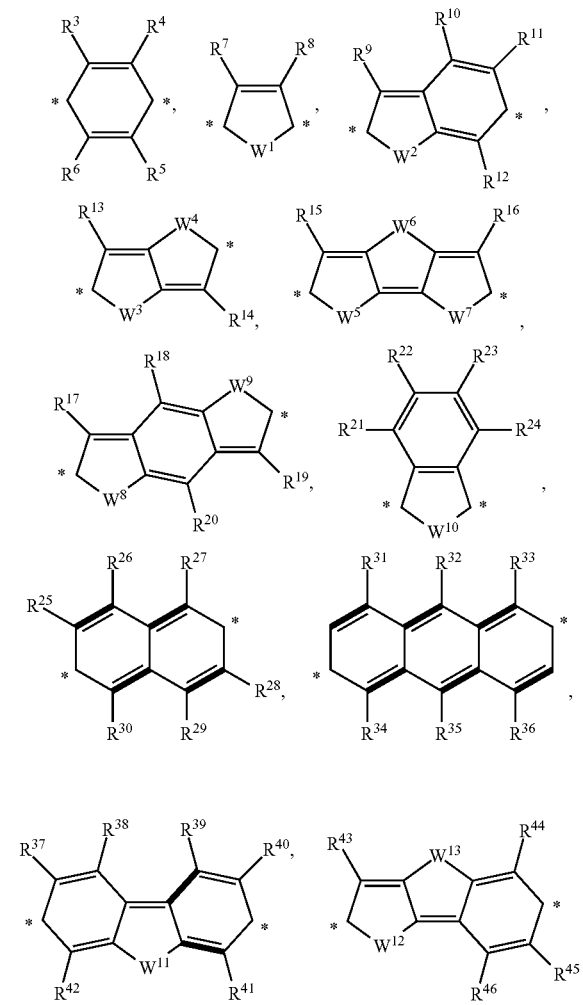

In Group 1, $W^1$ may be different from X, and may be S, Se, or Te, $W^2$ to $W^{13}$ may independently be S, Se, or Te, $R^3$ to $R^{46}$ may independently be hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof, $R^3$ to $R^{46}$ may independently be present or adjacent two of $R^3$ to $R^{46}$ may be linked to each other to provide a ring, and

* may be a linking point with Chemical Formula 1.

For example, when X is S, $W^1$ may be Se, or Te.

For example, when X is Se, $W^1$ may be S or Te.

For example, $W^2$ to $W^{11}$ may independently be S or Se, and for example, may independently be S.

For example, the compound represented by Chemical Formula 1 may be, for example, represented by one of Chemical Formulas 1A to 1I, but is not limited thereto.

[Chemical Formula 1A]
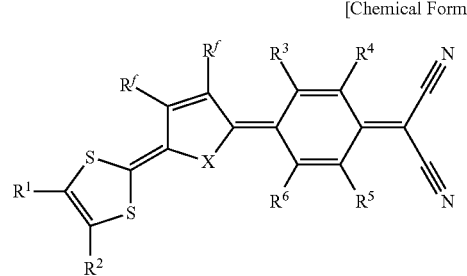

[Chemical Formula 1B]
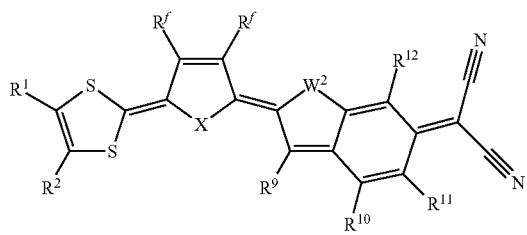

[Chemical Formula 1C]
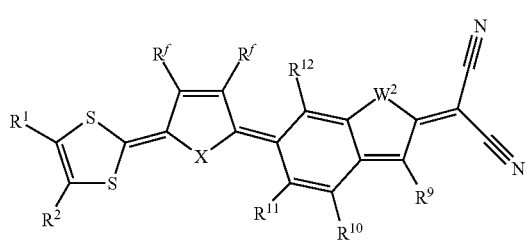

[Chemical Formula 1D]
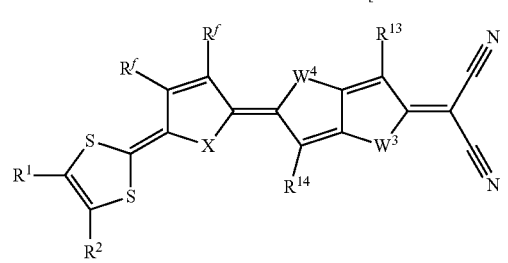

[Chemical Formula 1E]
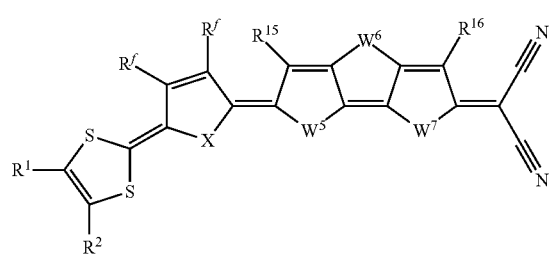

[Chemical Formula 1F]
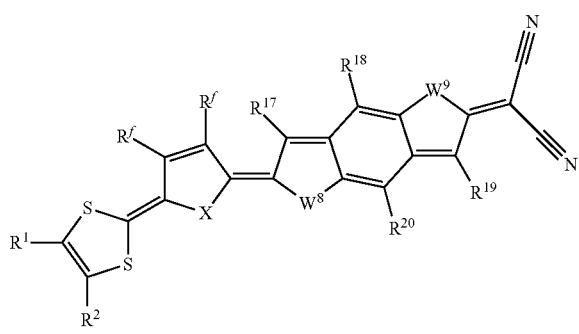

[Chemical Formula 1G]
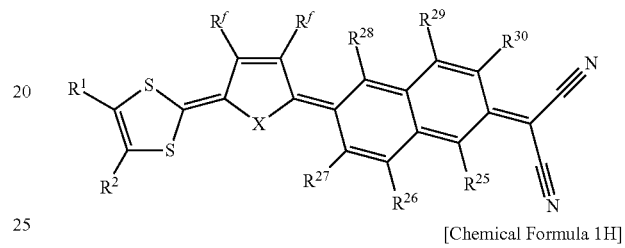

[Chemical Formula 1H]
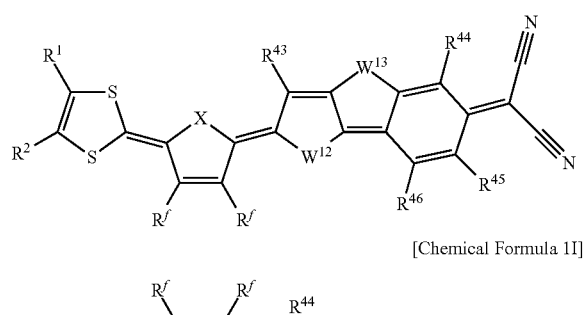

[Chemical Formula 1I]

In Chemical Formulas 1A to 1I, X, $W^2$ to $W^9$, $W^{12}$, $W^{13}$, $R^1$ to $R^6$, $R^9$ to $R^{20}$, $R^{25}$ to $R^{30}$, $R^{43}$ to $R^{46}$, and $R^f$ are the same as described above.

For example, the compound represented by Chemical Formula 1 may be represented by one of Chemical Formulas 1A-1 to 1I-1, but is not limited thereto.

[Chemical Formula 1A-1]
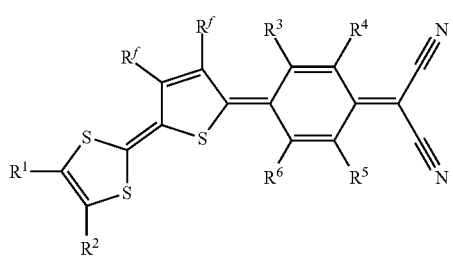

[Chemical Formula 1B-1]

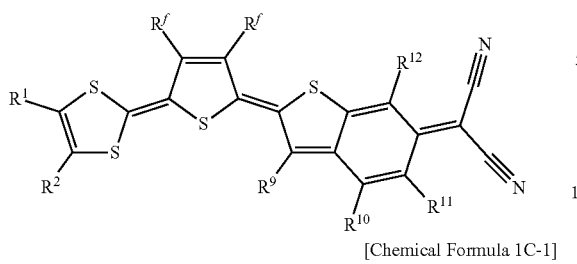

[Chemical Formula 1C-1]

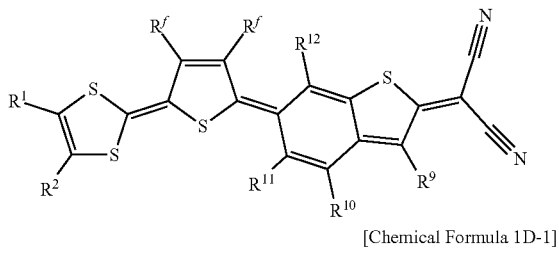

[Chemical Formula 1D-1]

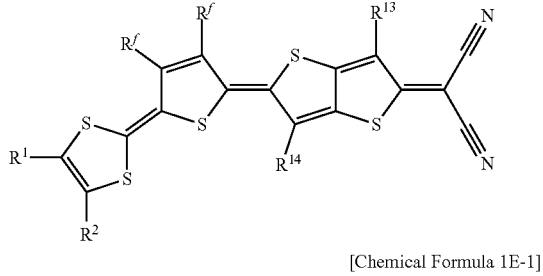

[Chemical Formula 1E-1]

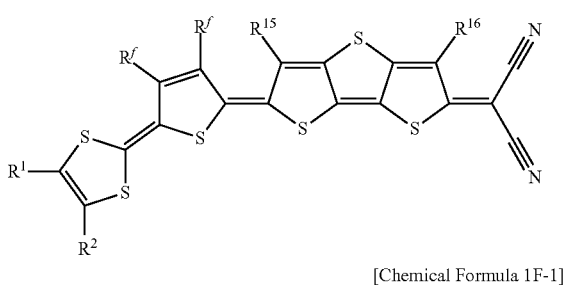

[Chemical Formula 1F-1]

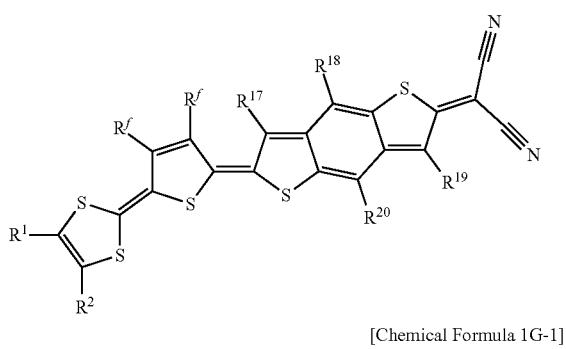

[Chemical Formula 1G-1]

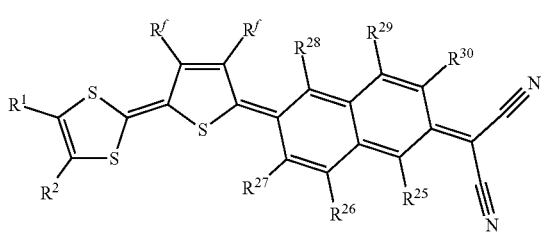

[Chemical Formula 1H-1]

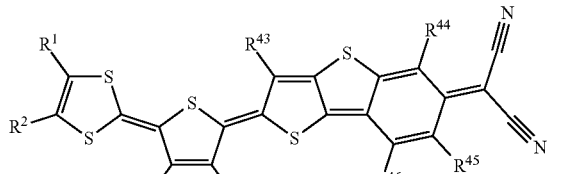

[Chemical Formula 1I-1]

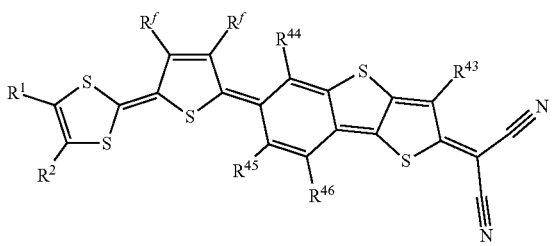

In Chemical Formulas 1A-1 to 1I-1, $R^1$ to $R^6$, $R^9$ to $R^{20}$, $R^{25}$ to $R^{30}$, $R^{43}$ to $R^{46}$, and $R^f$ are the same as described above.

The main absorption spectrum of the compound may be in the infrared absorption wavelength spectrum, wherein the infrared absorption wavelength spectrum may be for example greater than or equal to about 750 nm, greater than or equal to about 780 nm, greater than or equal to about 790 nm, greater than or equal to about 800 nm, greater than or equal to about 810 nm, greater than or equal to about 820 nm, greater than or equal to about 830 nm, greater than or equal to about 850 nm, greater than or equal to about 870 nm, greater than or equal to about 890 nm, greater than or equal to about 900 nm, greater than or equal to about 920 nm, greater than or equal to about 940 nm, greater than or equal to about 960 nm, greater than or equal to about 980 nm, greater than or equal to about 1000 nm, greater than or equal to about 1050 nm, or greater than or equal to about 1100 nm. For example, a peak absorption wavelength of the compound may be in a wavelength spectrum of about 750 nm to about 3000 nm, within the range, for example about 800 nm to about 3000 nm, for example about 750 nm to about 2500 nm, for example about 780 nm to about 2200 nm, for example about 790 nm to about 2100 nm, for example about 800 nm to about 2000 nm, for example about 810 nm to about 2000 nm, for example about 820 nm to about 2000 nm, for example about 830 nm to about 2000 nm, for example about 850 nm to about 2000 nm, for example about 870 nm to about 2000 nm, for example about 890 nm to about 2000 nm, for example about 900 nm to about 2000 nm, for example about 920 nm to about 2000 nm, for example about 940 nm to about 2000 nm, for example about 960 nm to about 2000 nm, for example about 980 nm to about 2000 nm, for example about 1000 nm to about 2000 nm, for example about 1050 nm to about 2000 nm, or for example about 1100 nm to about 2000 nm.

The compound may exhibit good photoelectric conversion properties, and thus may be effectively used as a photoelectric conversion material for an infrared sensor. For example, the energy bandgap of the compound may be, for example, about 0.5 eV to about 1.5 eV, and within the range, about 0.6 eV to about 1.4 eV, about 0.7 eV to about 1.3 eV, or about 0.8 eV to about 1.2 eV. For example, the HOMO energy level of the compound may be, for example, about 4.0 eV to about 5.5 eV, and within the range, about 4.2 eV to about 5.3 eV, about 4.4 eV to about 5.1 eV, or about 4.5 eV to about 5.0 eV.

On the other hand, the compound has good heat resistance, and thus may prevent or reduce thermal decomposition during deposition, and thus may be repeatedly deposited. The compound may be thermally or vacuum deposited and may be deposited, for example, by sublimation. For example, deposition by sublimation may be confirmed by thermogravimetric analysis (TGA), and at a thermogravimetric analysis at a pressure of less than or equal to about 10 Pa, a temperature at which a 10% weight loss relative to an initial weight may be less than or equal to about 450° C. and a temperature at which a 50% weight loss relative to an initial weight may be less than or equal to about 500° C. For example, at a thermogravimetric analysis at a pressure of less than or equal to about 10 Pa, a temperature at which a 10% weight loss relative to an initial weight of the compound may be for example about 230° C. to about 450° C. and a temperature at which a 50% weight loss relative to an initial weight may be about 300° C. to about 500° C.

The compound may be deposited to be prepared in the form of a film. Accordingly, in some example embodiments, a film may be provided where the film comprises the aforementioned compound. The film may have similar or same properties as described herein with regard to the compound. For example, the film that includes the compound may have a peak absorption wavelength in a wavelength spectrum of 800 nm to about 3000 nm. The film may have a greatly larger dimension in an in-plane direction (e.g., an xy direction) of the film, that is, a width and a length of the film, than a dimension in a depth direction (e.g., a z direction) of the film, that is, a thickness of the film. For example, the thickness of the film may be about 1 nm to about 100 µm, about 1 nm to about 80 µm, about 1 nm to about 50 µm, about 1 nm to about 40 µm, about 1 nm to about 30 µm, about 1 nm to about 20 µm, or about 1 nm to about 10 µm.

The film may be applied to various fields requiring light absorption properties of an infrared wavelength spectrum, for example, an infrared-absorbing/blocking film.

The compound has simultaneously light absorption properties and photoelectric characteristics of the infrared wavelength spectrum and may be effectively used as a photoelectric conversion material of an infrared sensor.

The infrared sensor may be configured to sense at least some light (e.g., incident light) in the infrared wavelength spectrum, for example, selectively absorb at least part of the infrared wavelength spectrum of the incident light, and thus convert it (e.g., photoelectrically convert the selectively absorbed incident light) into electrical signals. The infrared sensor may exhibit an absorption spectrum having a peak absorption wavelength in the infrared wavelength spectrum, wherein the infrared wavelength spectrum is the same as described above. Each infrared sensor may independently include a photo-sensing device such as a photodiode or a photoelectric conversion device, and may be, for example, a photoelectric conversion device.

FIG. 1 is a cross-sectional view showing an example of an infrared sensor according to some example embodiments.

Referring to FIG. 1, an infrared sensor 100 according to some example embodiments may be an infrared photoelectric conversion device, and includes a first electrode 10 and a second electrode 20 facing each other, and an organic layer 30 between the first electrode 10 and the second electrode 20. The organic layer 30 may include the aforementioned compound.

A substrate (not shown) may be disposed under the first electrode 10 or on the second electrode 20 and may be in direct contact with at least one of the first electrode 10 or the second electrode 20. The substrate may be, for example, made of an inorganic material such as glass, an organic material such as polycarbonate, polymethylmethacrylate, polyethyleneterephthalate, polyethylenenaphthalate, polyamide, polyethersulfone, or a combination thereof, or a silicon wafer. The substrate may be a semiconductor substrate. The substrate may be omitted.

One of the first electrode 10 or the second electrode 20 is an anode and the other is a cathode. For example, the first electrode 10 may be an anode and the second electrode 20 may be a cathode. For example, the first electrode 10 may be a cathode and the second electrode 20 may be an anode.

At least one of the first electrode 10 or the second electrode 20 may be a (semi) light-transmitting electrode, and the (semi) light-transmitting electrode may be made of a conductive oxide such as indium tin oxide (ITO), indium zinc oxide (IZO), zinc oxide (ZnO), tin oxide (SnO), aluminum tin oxide (AlTO), and fluorine doped tin oxide (FTO) or a thin single layer or multiple layers of a metal thin film including silver (Ag), copper (Cu), aluminum (Al), magnesium (Mg), magnesium-silver (Mg—Ag), magnesium-aluminum (Mg—Al), or a combination thereof.

For example, both the first electrode 10 and the second electrode 20 may be (semi) light-transmitting electrodes. For example, the second electrode 20 may be a light receiving electrode disposed at a side that receives light (e.g., incident light).

As an example, one of the first electrode 10 or the second electrode 20 may be a (semi) light-transmitting electrode and the other may be a reflective electrode. The reflective electrode may include a reflective layer including an optically opaque material. The reflective layer may have a light transmittance of less than about 10%, less than or equal to about 8%, less than or equal to about 7%, less than or equal to about 5%, less than or equal to about 3%, or less than or equal to about 1%. The light transmittance of the reflective layer may be equal to or greater than 0%, equal to or greater than about 0.1%, equal to or greater than about 0.5%, equal to or greater than about 1%, or equal to or greater than about 5%. The reflective layer may have a reflectance of greater than or equal to about 10%, greater than or equal to about 20%, greater than or equal to about 30%, greater than or equal to about 50%, or greater than or equal to about 70%. The reflectance of the reflective layer may be equal to or less than 100%, equal to or less than about 99%, equal to or less than about 95%, equal to or less than about 90%, or equal to or less than about 80%. The optically opaque material may include a metal, a metal nitride, or a combination thereof, such as silver (Ag), copper (Cu), aluminum (Al), gold (Au), titanium (Ti), chromium (Cr), nickel (Ni), an alloy thereof, a nitride thereof (e.g., TiN), or a combination thereof, but is not limited thereto. The reflective layer may be one layer or two or more layers.

The organic layer 30 includes an infrared photoelectric conversion layer 31 and auxiliary layers 32 and 33 disposed on and/or under the infrared photoelectric conversion layer 31.

The infrared photoelectric conversion layer 31 is configured to absorb light (e.g., incident light) in an infrared wavelength spectrum and photoelectric convert the absorbed light into an electrical signal, and may include the aforementioned compound.

Such absorbing and photoelectric conversion of light in an infrared wavelength spectrum may be referred to herein as "sensing" and/or "detecting" said light in the infrared wavelength spectrum. The infrared photoelectric conversion layer 31 may include a p-type semiconductor and an n-type semiconductor forming a pn junction, and generate excitons by receiving light from the outside (e.g., an ambient environment external to the infrared sensor 100), and then separating the generated excitons into holes and electrons.

The p-type semiconductor and/or the n-type semiconductor may be a light absorbing material configured to absorb light in at least a portion of wavelength spectrum. For example, the aforementioned compound may be used (e.g., included) in the infrared photoelectric conversion layer 31 as a p-type semiconductor or an n-type semiconductor in the infrared photoelectric conversion layer 31, and the infrared photoelectric conversion layer 31 may further include a counterpart material (also referred to herein as a counter material) forming a pn junction with the compound.

The counter material may be for example a light absorbing material or a non-light absorbing material. For example, the aforementioned compound may be used as a p-type semiconductor, and the infrared photoelectric conversion layer 31 may further include an n-type semiconductor forming a pn junction with the compound. The n-type semiconductor may include fullerene or a fullerene derivative. For example, the aforementioned compound may be used as an n-type semiconductor, and the infrared photoelectric conversion layer 31 may further include a p-type semiconductor forming a pn junction with the compound.

For example, the infrared photoelectric conversion layer 31 may include an intrinsic layer (I layer) 31$i$ in which a p-type semiconductor and an n-type semiconductor are co-deposited, where one of the p-type semiconductor or the n-type semiconductor includes the aforementioned compound represented by Chemical Formula 1 and the other of the p-type semiconductor or the n-type semiconductor includes the aforementioned counter material. The intrinsic layer 31$i$ may be a blended layer in which a p-type semiconductor and an n-type semiconductor are blended in a form of bulk heterojunction.

For example, the p-type semiconductor and the n-type semiconductor in the intrinsic layer (e.g., the aforementioned compound and the counter material) may be included in a volume ratio (thickness ratio) of about 1:9 to about 9:1, within the range for example a volume ratio (thickness ratio) of about 2:8 to about 8:2, about 3:7 to about 7:3, about 4:6 to about 6:4, or about 5:5.

For example, the p-type semiconductor in the intrinsic layer 31$i$ (which may include one of the compound or the counter material) may be included in less than that of the n-type semiconductor (which may include the other of the compound or the counter material). For example, the composition ratio (volume ratio or thickness ratio) of the p-type semiconductor to the n-type semiconductor in the intrinsic layer 31$i$ may be about 0.10 to about 0.90. The composition ratio of the p-type semiconductor to the n-type semiconductor may be, for example, about 0.10 to about 0.80, about 0.10 to about 0.70, about 0.10 to about 0.50, or about 0.10 to about 0.30.

The infrared photoelectric conversion layer 31 may further include a p-type layer 31$p$ and/or an n-type layer 31$n$ in addition to the intrinsic layer 31$i$. However, example embodiments are not limited thereto. For example, in some example embodiments the p-type layer 31$p$ and the n-type layer 31$n$ are absent such that the intrinsic layer 31$i$ comprises the entire infrared photoelectric conversion layer 31. In some example embodiments the infrared photoelectric conversion layer 31 comprises a single layer (e.g., a single layer that includes one material or one combination of materials) and does not include additional layers. The p-type layer 31$p$ may include the aforementioned p-type semiconductor (which may include one of the compound or the counter material) and the n-type layer 31$n$ may include the aforementioned n-type semiconductor (which may include the other of the compound or the counter material). For example, it (e.g., the infrared photoelectric conversion layer 31) may be included in various combinations such as a p-type layer/I layer, an I-layer/n-type layer, and a p-type layer/I-layer/n-type layer.

The main absorption spectrum of the compound may be in the infrared absorption wavelength spectrum, wherein the infrared absorption wavelength spectrum may be, for example, greater than or equal to about 800 nm, greater than or equal to about 810 nm, greater than or equal to about 820 nm, greater than or equal to about 830 nm, greater than or equal to about 850 nm, greater than or equal to about 870 nm, greater than or equal to about 890 nm, greater than or equal to about 900 nm, greater than or equal to about 920 nm, greater than or equal to about 940 nm, greater than or equal to about 960 nm, greater than or equal to about 980 nm, greater than or equal to about 1000 nm, greater than or equal to about 1050 nm, or greater than or equal to about 1100 nm. For example, the infrared photoelectric conversion layer 31, and thus the infrared sensor 100, may have a peak absorption wavelength that belongs to a wavelength spectrum of about 800 nm to about 3000 nm, within the range for example about 810 nm to about 2500 nm, for example about 820 nm to about 2200 nm, for example about 830 nm to about 2100 nm, for example about 840 nm to about 2000 nm, for example about 850 nm to about 2000 nm, for example about 860 nm to about 2000 nm, for example about 870 nm to about 2000 nm, for example about 880 nm to about 2000 nm, for example about 890 nm to about 2000 nm, for example about 900 nm to about 2000 nm, for example about 920 nm to about 2000 nm, for example about 940 nm to about 2000 nm, for example about 960 nm to about 2000 nm, for example about 980 nm to about 2000 nm, for example about 990 nm to about 2000 nm, for example about 1000 nm to about 2000 nm, for example about 1050 nm to about 2000 nm, or for example about 1100 nm to about 2000 nm.

The infrared photoelectric conversion layer 31 may have a thickness of about 30 nm to about 500 nm, within the above range, about 50 nm to about 400 nm, about 80 nm to about 300 nm, about 100 nm to about 200 nm, or about 140 nm to about 160 nm.

The organic layer 30 may further include auxiliary layers 32 and 33. The auxiliary layers 32 and 33 may be between the first electrode 10 and the infrared photoelectric conversion layer 31 and/or between the second electrode 20 and the infrared photoelectric conversion layer 31, respectively. In some example embodiments, one or both of the auxiliary layers 32 and/or 33 may be omitted.

Accordingly, it will be understood that the infrared sensor 100 may include an auxiliary layer (e.g., 32 and/or 33) that is at least one of between the first electrode 10 and the infrared photoelectric conversion layer 31 or between the second electrode 20 and the infrared photoelectric conversion layer 31.

For example, the auxiliary layers 32 and 33 may be charge auxiliary layers to improve transfer of holes and electrons separated from the infrared photoelectric conversion layer 31 to increase efficiency of the infrared sensor 100. The auxiliary layers 32 and 33 may include at least one selected from a hole injecting layer (HIL) that facilitates hole injection, a hole transporting layer (HTL) that facilitates hole transport, an electron blocking layer (EBL) that blocks the movement of electrons, an electron injecting layer (EIL) that facilitates electron injection, an electron transporting layer (ETL) that facilitates the transport of electrons, and a hole blocking layer (HBL) that blocks the movement of holes.

As an example, the auxiliary layers 32 and 33 may be light absorption auxiliary layers, and may be disposed on and/or under the infrared photoelectric conversion layer 31 to increase a quantity of light absorbed by the infrared photoelectric conversion layer 31 and thereby to improve light absorption properties. For example, one of the auxiliary layers 32 or 33 may include the aforementioned compound. For example, one of the auxiliary layers 32 or 33 may include a fullerene or a fullerene derivative.

The auxiliary layers 32 and 33 may include, for example, an organic material, an inorganic material, or an organic-inorganic material.

For example, at least one of the auxiliary layers 32 or 33 may include a low molecular weight compound, for example, may include the aforementioned compound.

For example, at least one of the auxiliary layers 32 or 33 may include a low molecular weight compound, for example, a carbazole-containing compound.

For example, at least one of the auxiliary layers 32 or 33 may include a polymer.

For example, one of the auxiliary layers 32 or 33 may include an inorganic material, for example, a lanthanide element such as ytterbium (Yb); calcium (Ca); potassium (K); barium (Ba); magnesium (Mg); lithium fluoride (LiF); or an alloy thereof.

For example, at least one of the auxiliary layers 32 or 33 may include fullerene or a fullerene derivative.

For example, one of the auxiliary layers 32 or 33 may include an inorganic material, and may include a metal oxide such as molybdenum oxide, tungsten oxide, or nickel oxide.

For example, at least one of the auxiliary layers 32 or 33 may include the aforementioned compound represented by Chemical Formula 1.

In some example embodiments, an infrared sensor 100 may include the infrared photoelectric conversion layer 31 and at least one of the auxiliary layers 32 or 33, where at least one of the infrared photoelectric conversion layer 31 or the at least one of the auxiliary layers 32 or 33 includes the aforementioned compound represented by Chemical Formula 1. For example, in some example embodiments, the at least one of the auxiliary layers 32 or 33 may include the aforementioned compound represented by Chemical Formula 1 while the infrared photoelectric conversion layer 31 may not include the aforementioned compound represented by Chemical Formula 1.

The auxiliary layers 32 and 33 may have each independently a thickness of about 1 nm to about 200 nm, within the range, about 5 nm to about 200 nm, about 5 nm to about 180 nm, or about 5 nm to about 150 nm.

At least one of the auxiliary layers 32 or 33 may be omitted.

The infrared sensor 100 may further include an anti-reflection layer (not shown) on the first electrode 10 or under the second electrode 20. The anti-reflection layer may be disposed at the side to which the light is incident to reduce a reflectance of the incident light, thereby further improving light absorption. For example, when light is incident to the first electrode 10, the anti-reflection layer may be under the first electrode 10, and when light is incident to the second electrode 20, the anti-reflection layer may be disposed on the second electrode 20.

The anti-reflection layer may include, for example a material having a refractive index of about 1.6 to about 2.5, and may include for example at least one of metal oxide, metal sulfide, or an organic material having a refractive index within the ranges.

The anti-reflection layer may include, for example a metal oxide such as aluminum-containing oxide, molybdenum-containing oxide, tungsten-containing oxide, vanadium-containing oxide, rhenium-containing oxide, niobium-containing oxide, tantalum-containing oxide, titanium-containing oxide, nickel-containing oxide, copper-containing oxide, cobalt-containing oxide, manganese-containing oxide, chromium-containing oxide, tellurium-containing oxide, or a combination thereof; metal sulfide such as zinc sulfide; or an organic material such as an amine derivative, but is not limited thereto.

The infrared sensor 100 may further include an encapsulation film (not shown) under the first electrode 10 or on the second electrode 20 (e.g., in direct contact with at least one of the first electrode 10 or the second electrode 20).

The infrared sensor 100 may further include an optical auxiliary layer (not shown) under the first electrode 10 or on the second electrode 20 (e.g., in direct contact with at least one of the first electrode 10 or the second electrode 20). The optical auxiliary layer may be configured to selectively transmit light in a particular (or, alternatively, predetermined) wavelength spectrum among incident light and may be configured to reflect and/or absorb light in a wavelength spectrum other than the particular (or, alternatively, predetermined) wavelength spectrum. That is, the optical auxiliary layer may be a selective transmission layer, for example, may be a semi-transmissive layer.

The optical auxiliary layer may include, for example, a first optical auxiliary layer and a second optical auxiliary layer having different refractive indices. The first optical auxiliary layer may be for example a high refractive index layer and the second optical auxiliary layer may be for example a low refractive index layer. The refractive index (e.g., at about 800 nm to about 1200 nm) of the high refractive index layer may be, for example, greater than or equal to about 1.55 or about 1.55 to about 1.90, and the refractive index (e.g., at about 800 nm to about 1200 nm) of the low refractive index layer may be, for example, less than about 1.55 or greater than or equal to about 1.20 and less than about 1.55. For example, the first optical auxiliary layer may be an aluminum oxide, an organic buffer material, an inorganic buffer material, or a combination thereof, and the second optical auxiliary layer may be a silicon oxide, a silicon nitride, a silicon oxynitride, or a combination thereof, but are limited thereto.

In the infrared sensor 100, when light is incident from the side of the first electrode 10 or the second electrode 20 and the infrared photoelectric conversion layer 31 is configured to absorb light in the infrared wavelength spectrum, excitons may be generated therein. The generated excitons are separated into holes and electrons in the infrared photoelectric conversion layer 31. The separated holes may move towards the anode which is one of the first electrode 10 or the second electrode 20, and the separated electrons may move towards the cathode which is the other of the first electrode 10 or the second electrode 20, and thus an electrical signal may be obtained.

For example, when the infrared sensor 100 includes a reflective electrode and a (semi) light-transmitting electrode as the first electrode 10 and the second electrode 20, a microcavity structure may be formed. Due to the microcavity structure, incident light may be repeatedly reflected between the reflective electrode and the (semi) light-transmitting electrode which are separated by a particular (or, alternatively, predetermined) optical path length to enhance light having a particular (or, alternatively, predetermined) wavelength spectrum. For example, light having a particular (or, alternatively, predetermined) wavelength spectrum among the incident light may be modified by repeatedly reflecting between the reflective electrode and the (semi) light-transmitting electrode, and among the modified light, light of a wavelength spectrum corresponding to a resonance wavelength of the microcavity may be enhanced to exhibit amplified photoelectric conversion characteristics in a narrow wavelength spectrum.

Due to this microcavity structure, an absorption spectrum of the infrared photoelectric conversion layer 31 may further include a sub-absorption spectrum in addition to the aforementioned main absorption spectrum. The sub-absorption spectrum may be located in a longer wavelength spectrum than the main absorption spectrum and a peak wavelength of the sub-absorption spectrum may be for example greater than or equal to about 1000 nm, greater than or equal to about 1050 nm, greater than or equal to about 1100 nm, greater than or equal to about 1150 nm, greater than or equal to about 1200 nm, for example about 1000 nm to about 3000 nm, about 1050 nm to about 3000 nm, about 1100 nm to about 3000 nm, about 1150 nm to about 3000 nm, or about 1200 nm to about 3000 nm.

The infrared sensor 100 may be applied to various fields for sensing light in the infrared wavelength spectrum, for example, an image sensor for improving sensitivity in a low light environment, a sensor for increasing detection capability of 3D images by broadening the dynamic range for detailed black and white contrast, a security sensor, a vehicle sensor, a biometric sensor, or the like, and the biometric sensor may be, for example, an iris sensor; a distance sensor; a fingerprint sensor; a biosignal sensor such as a PPG sensor; or a living body imaging sensor such as a blood vessel imaging sensor, but is not limited thereto. The infrared sensor may be applied to, for example, a CMOS infrared sensor or a CMOS image sensor.

The CMOS infrared sensor may include a plurality of pixels, and at least some of the plurality of pixels may include the aforementioned infrared sensor 100. The CMOS infrared sensor may include one or a plurality of infrared sensors 100 arranged in an array form along a row and/or column on a semiconductor substrate.

Accordingly, an image sensor may include the infrared sensor 100 of FIG. 1 and may further include a semiconductor substrate, where the infrared sensor 100 is on the semiconductor substrate (e.g., the first electrode 10 or the second electrode 20 may be in direct contact with the semiconductor substrate).

Figure 2:
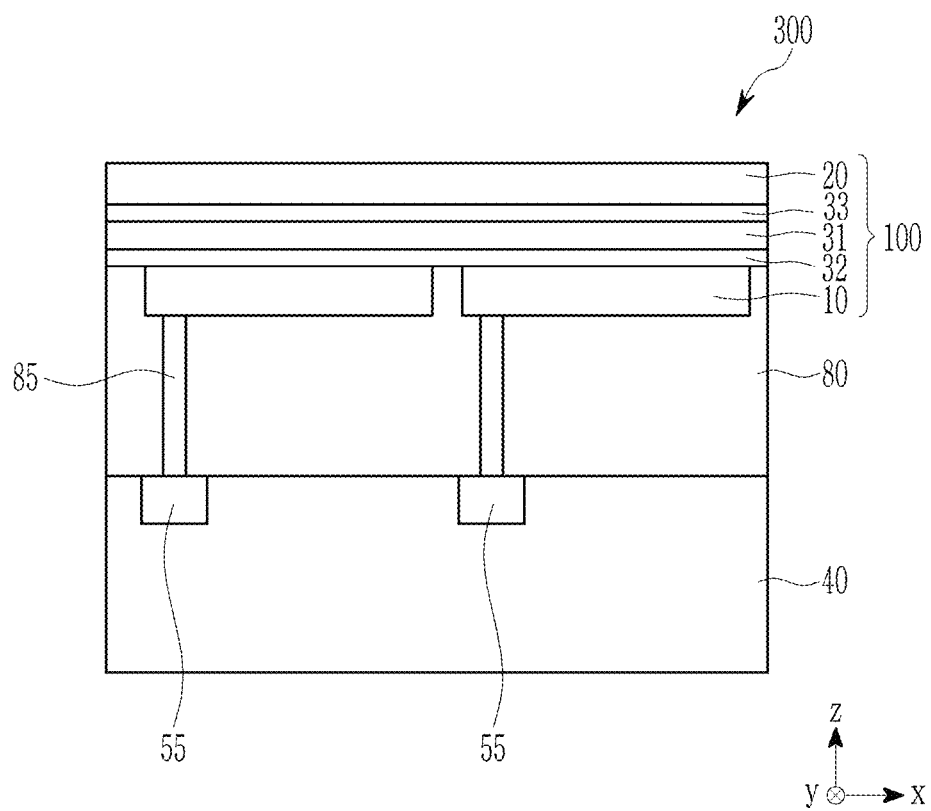
FIG. 2 is a cross-sectional view showing an example of a CMOS infrared sensor according to some example embodiments.

FIG. 2 is a cross-sectional view showing an example of a CMOS infrared sensor according to some example embodiments.

The CMOS infrared sensor 300 according to some example embodiments includes a semiconductor substrate 40, an insulating layer 80, and an infrared sensor 100.

The semiconductor substrate 40 may be a silicon substrate and is integrated with a transmission transistor (not shown) and a charge storage 55. The charge storage 55 may be integrated in each pixel. The charge storage 55 is electrically connected to the infrared sensor 100 and information of the charge storage 55 may be transmitted by the transmission transistor.

A metal wire (not shown) and a pad (not shown) are formed on the semiconductor substrate 40. In order to decrease signal delay, the metal wire and pad may be made of a metal having low resistivity, for example, aluminum (Al), copper (Cu), silver (Ag), and alloys thereof, but is not limited thereto. However, it is not limited to the structure and the metal wire and pads may be disposed under the semiconductor substrate 40.

The insulating layer 80 is formed on the metal wire and the pad. The insulating layer 80 may be made of an inorganic insulating material such as a silicon oxide and/or a silicon nitride, or a low dielectric constant (low K) material such as SiC, SiCOH, SiCO, and SiOF. The insulating layer 80 has a trench 85 exposing the charge storage 55. The trench may be filled with fillers.

The aforementioned infrared sensor 100 is formed on the insulating layer 80. The infrared sensor 100 may include a first electrode 10, a second electrode 20, an infrared photoelectric conversion layer 31, and optionally auxiliary layers 32 and 33 as described above.

Both the first electrode 10 and the second electrode 20 may be transparent electrodes, and the descriptions for the first electrode 10, the second electrode 20, the infrared photoelectric conversion layer 31, and the auxiliary layers 32 and 33 are the same as described above. The light in the infrared wavelength spectrum of the light incident from the side of the second electrode 20 may be effectively absorbed by the infrared photoelectric conversion layer 31 to be photoelectrically converted.

Focusing lens (not shown) may be further formed on the infrared sensor 100. The focusing lens may control a direction of incident light and gather the light in one region. The focusing lens may have a shape of, for example, a cylinder or a hemisphere, but is not limited thereto.

The infrared sensor 100 or the CMOS infrared sensor 300 may be included in a combination sensor including a plurality of sensors having different functions.

At least one of a plurality of sensors having different functions may be a biometric sensor. The biometric sensor may be for example an iris sensor, a depth sensor, a fingerprint sensor, or a blood vessel distribution sensor, but is not limited thereto. For example, one of a plurality of sensors having different functions may be an iris sensor and the other one may be a depth sensor.

For example, a plurality of sensors having different functions may include a first infrared sensor configured to sense light in an infrared region having a first wavelength ($\lambda_1$) and a second infrared sensor configured to sense infrared light having a second wavelength ($\lambda_2$) within an infrared wavelength spectrum.

The first wavelength ($\lambda_1$) and the second wavelength ($\lambda_2$) may differ from each other within the infrared wavelength spectrum. For example, a difference between the first wavelength ($\lambda_1$) and the second wavelength ($\lambda_2$) may be greater than or equal to about 30 nm, within the range greater than or equal to about 50 nm, greater than or equal to about 70 nm, greater than or equal to about 80 nm, or greater than or equal to about 90 nm. Said difference may be equal to or less than about 500 nm, equal to or less than about 400 nm, equal to or less than about 300 nm, equal to or less than about 200 nm, equal to or less than about 150 nm, equal to or less than about 100 nm, or equal to or less than about 95 nm.

For example, one of the first wavelength ($\lambda_1$) or the second wavelength ($\lambda_2$) may be within a wavelength spectrum of about 750 nm to about 1000 nm, and the other of the first wavelength ($\lambda_1$) or the second wavelength ($\lambda_2$) may be within a wavelength spectrum of about 800 nm to about 1500 nm.

Figure 3:
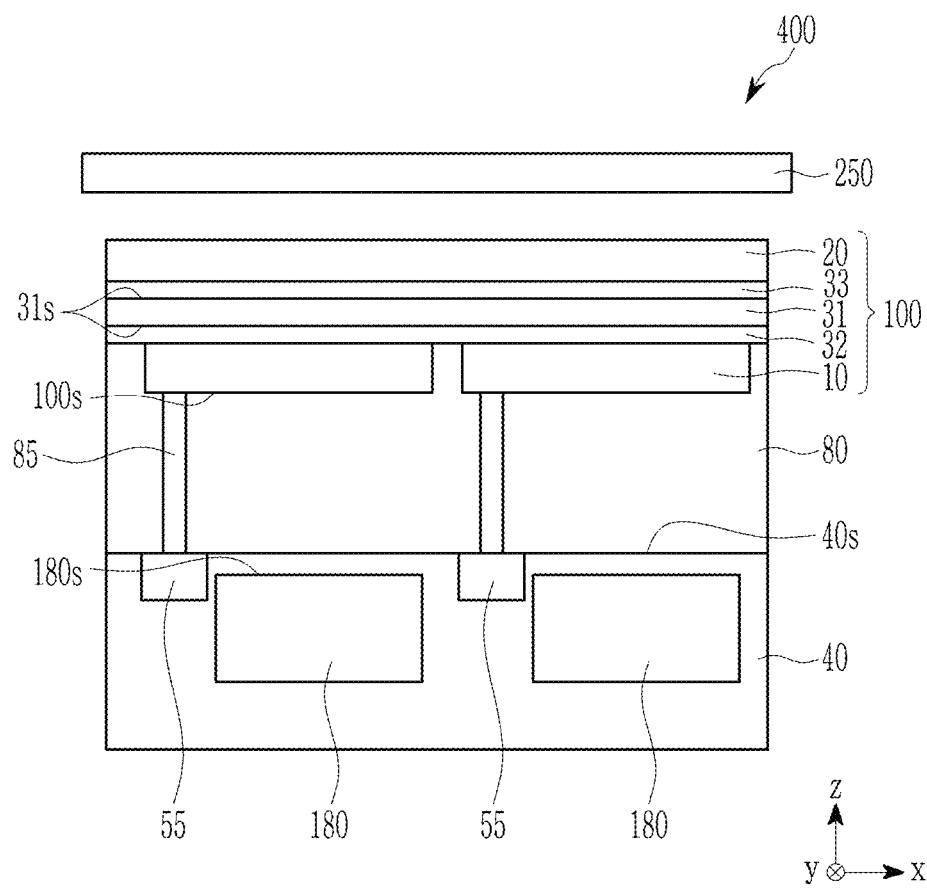
FIG. 3 is a cross-sectional view showing an example of a combination sensor according to some example embodiments.

FIG. 3 is a cross-sectional view showing an example of a combination sensor according to some example embodiments.

The combination sensor 400 according to some example embodiments includes an optical filter 250; an infrared sensor 100; an insulating layer 80; and a semiconductor substrate 40 in which the photodiode 180 and the charge storage 55 are integrated. The infrared sensor 100 and the photodiode 180 are stacked along the depth direction (e.g., z direction) of the semiconductor substrate 40. Restated, the infrared sensor 100 and the photodiode 180 may be understood to be stacked together in a depth direction (e.g., z direction) that is perpendicular to a plane in which the infrared sensor 100 extends and/or an in-plane direction of the infrared sensor 100 (e.g., x and y directions) and/or is perpendicular to an upper surface of the semiconductor substrate 40 opposing surfaces 100s, 180s of the infrared sensor 100 and the photodiode 180 and is further perpendicular to at least opposite surfaces 31s of the infrared photoelectric conversion layer 31, opposite surfaces of the first electrode 10, and opposite surfaces of the second electrode 20 of the infrared sensor 100.

The optical filter 250 may be disposed at the front side of the combination sensor 400, and may be configured to selectively transmit light in the infrared wavelength spectrum including the first wavelength ($\lambda_1$) and light in the infrared wavelength spectrum including the second wavelength ($\lambda_2$) and may be configured to block and/or absorb other light. Here, the other light may also include ultraviolet and visible light.

The infrared sensor 100 may be a first infrared sensor, and a detailed description is the same as described above.

The photodiode 180 may be a second infrared sensor and may be integrated in the semiconductor substrate 40. The semiconductor substrate 40 may be, for example, a silicon substrate, and a photodiode 180, a charge storage 55, and a transfer transistor (not shown) are integrated therein.

The infrared sensor 100 may be configured to detect (e.g., absorb and/or photoelectrically convert) incident light in a first wavelength spectrum, of the infrared wavelength spectrum, that includes the first wavelength ($\lambda_1$) of the infrared wavelength spectrum. The photodiode 180 may be configured to detect (e.g., absorb and/or photoelectrically convert) incident light in a second wavelength spectrum, of the infrared wavelength spectrum, that includes the second wavelength ($\lambda_2$) of the infrared wavelength spectrum. The second wavelength spectrum may be a shorter wavelength spectrum or a longer wavelength spectrum than the first wavelength spectrum. Restated, wavelengths in the second wavelength spectrum (e.g., the second wavelength ($\lambda_2$) of the infrared wavelength spectrum) may be shorter or longer wavelengths than wavelengths in the first wavelength spectrum (e.g., the first wavelength ($\lambda_1$) of the infrared wavelength spectrum). The first and second wavelength spectrums may partially overlap or may not overlap at all. In some example embodiments, a difference between closest wavelengths of non-overlapping first and second wavelength spectrums may be greater than or equal to about 30 nm, within the range greater than or equal to about 50 nm, greater than or equal to about 70 nm, greater than or equal to about 80 nm, or greater than or equal to about 90 nm. Said difference may be equal to or less than about 500 nm, equal to or less than about 400 nm, equal to or less than about 300 nm, equal to or less than about 200 nm, equal to or less than about 150 nm, equal to or less than about 100 nm, or equal to or less than about 95 nm.

The light entering the photodiode 180 is light that has passed the optical filter 250 and the infrared sensor 100 and may be light in a particular (or, alternatively, predetermined) region including the second wavelength ($\lambda_2$) of the infrared wavelength spectrum. The infrared light in a particular (or, alternatively, predetermined) region including the first wavelength ($\lambda_1$) may be substantially all absorbed in the infrared photoelectric conversion layer 31 of the infrared sensor 100 and thus not reach the photodiode 180. Accordingly, a separate filter for wavelength selectivity of the light entering the photodiode 180 may not be needed. However, in case that the light in a particular (or, alternatively, predetermined) region including the first wavelength ($\lambda_1$) in the infrared wavelength spectrum is not all absorbed in the infrared photoelectric conversion layer 31, a separate filter (not shown) may be disposed between the infrared sensor 100 and the photodiode 180. The first wavelength ($\lambda_1$) may be a peak absorption wavelength of (e.g., exhibited by) the first infrared sensor (e.g., infrared sensor 100), and the second wavelength ($\lambda_2$) may be a peak absorption wavelength of the second infrared sensor (e.g., photodiode).

The combination sensor 400 according to some example embodiments may not only work as a combination sensor by including two infrared sensors performing two different functions but also greatly improve sensitivity by stacking two sensors performing different functions in each pixel to double the number of pixels of acting each infrared sensor with maintaining the same size.

Figure 4:
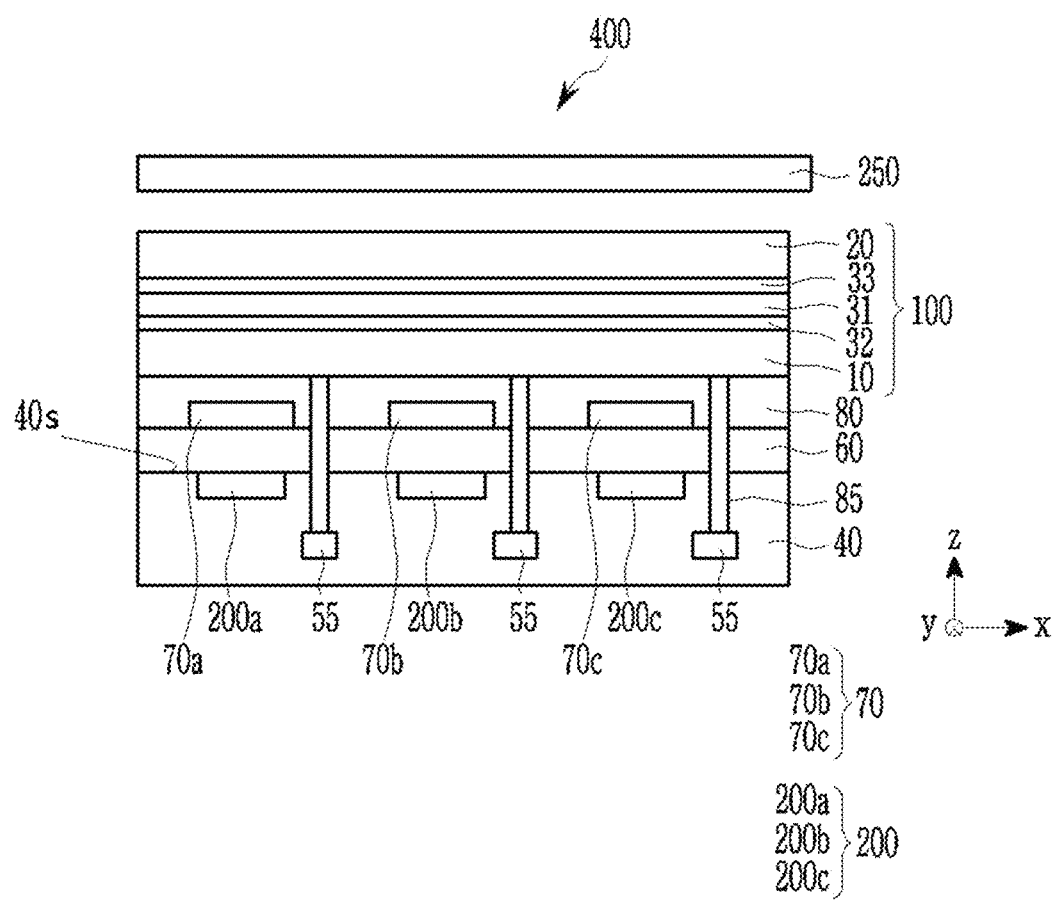
FIG. 4 is a cross-sectional view showing another example of a combination sensor according to some example embodiments.

FIG. 4 is a cross-sectional view showing another example of a combination sensor according to some example embodiments.

Referring to FIG. 4, the combination sensor 400 according to some example embodiments includes an infrared sensor 100, a visible light sensor 200, and an optical filter 250.

As described above, the infrared sensor 100 includes a first electrode 10, a second electrode 20, an infrared photoelectric conversion layer 31, and optionally auxiliary layers 32 and 33. Details are the same as described above.

The visible light sensor 200 is configured to sense (e.g., detect) at least a portion of incident light in a visible light wavelength spectrum, and may be a photodiode integrated in the semiconductor substrate 40. The visible light sensor 200 may be integrated in the semiconductor substrate 40 and may include a blue sensor 200a configured to sense light in a blue wavelength spectrum, a green sensor 200b configured to sense light in a green wavelength spectrum, and a red sensor 200c configured to sense light in a red wavelength spectrum. As shown in FIG. 4, each of the blue sensor 200a, the green sensor 200b, and the red sensor 200c may be a photodiode that is integrated in the semiconductor substrate 40, such that the blue sensor 200a, the green sensor 200b, and the red sensor 200c are located within a volume space defined by outer surfaces of the semiconductor substrate 40 and may be partially or completely enclosed within an interior of the semiconductor substrate 40. The blue sensor 200a may be integrated in the blue pixel, the green sensor 200b may be integrated in the green pixel, and the red sensor 200c may be integrated in the red pixel.

The semiconductor substrate 40 may be, for example, a silicon substrate, and a visible light sensor 200, a charge storage 55, and a transfer transistor (not shown) are integrated therein. The visible light sensor 200 may be configured to sense light in the visible light wavelength spectrum that has passed through the optical filter 250, the infrared sensor 100, and the color filter layer 70, and the sensed information may be transmitted by the transmission transistor. The charge storage 55 is electrically connected to the infrared sensor 100.

A metal wire (not shown) and a pad (not shown) are formed on the semiconductor substrate 40. In order to decrease signal delay, the metal wire and pad may be made of a metal having low resistivity, for example, aluminum (Al), copper (Cu), silver (Ag), and alloys thereof, but is not limited thereto. However, it is not limited to the structure and the metal wire and pads may be disposed under the blue sensor 200a, the green sensor 200b, and the red sensor 200c.

The lower insulating layer 60 is formed on the semiconductor substrate 40. The lower insulating layer 60 may be made of an inorganic insulating material such as a silicon oxide and/or a silicon nitride, or a low dielectric constant (low K) material such as SiC, SiCOH, SiCO, and SiOF.

The color filter layer 70 is formed on the lower insulating layer 60. The color filter layer 70 may include a blue filter 70a configured to selectively transmit light in the blue wavelength spectrum, a green filter 70b configured to selectively transmit light in a green wavelength spectrum, and a red filter 70c configured to selectively transmit light in the red wavelength spectrum. The blue filter 70a, the green filter 70b, and the red filter 70c are each overlapped with the blue sensor 200a, the green sensor 200b, and the red sensor 200c in the depth direction (e.g., the z direction). The blue filter 70a may be configured to selectively transmit light in a blue wavelength spectrum, the green filter 70b may be configured to selectively transmit light in a green wavelength spectrum, and the red filter 70c may be configured to selectively transmit light in the red wavelength spectrum. The transmitted light of the blue wavelength spectrum may flow into the blue sensor 200a, the transmitted light of a green wavelength spectrum may flow into the green sensor 200b, and the transmitted light of the red wavelength spectrum may flow into the red sensor 200c. However, the present disclosure is not limited thereto, but at least one of the blue filter 70a, the green filter 70b, or the red filter 70c may be replaced with a yellow filter, a cyan filter, or a magenta filter. Herein, the color filter layer 70 is disposed between the infrared sensor 100 and the visible light sensor 200 but not limited thereto and may be disposed on the infrared sensor 100. For example, the upper insulating layer 80 and color filter layer 70 may be between the infrared sensor 100 and the optical filter 250.

An upper insulating layer 80 (also referred to herein as an insulating layer 80) is formed on the color filter layer 70. The upper insulating layer 80 may be for example a planarization layer. The lower insulating layer 60 and the upper insulating layer 80 may have has a trench 85 exposing the charge storage 55. The trench 85 may be filled with fillers. At least one of the lower insulating layer 60 or the upper insulating layer 80 may be omitted.

The optical filter 250 is disposed on the visible light sensor 200 and the infrared sensor 100 and specifically, on the whole surface of the visible light sensor 200 and the infrared sensor 100. The optical filter 250 may be configured to selectively transmit light of a wavelength sensed in the visible light sensor 200 and light of a wavelength sensed in the infrared sensor 100 but reflect or absorb and thus block light of the other wavelengths.

Focusing lens (not shown) may be further formed on the upper or lower surface of the optical filter 250. The focusing lens may control a direction of incident light and gather the light in one region. The focusing lens may have a shape of, for example, a cylinder or a hemisphere, but is not limited thereto.

Figure 5:
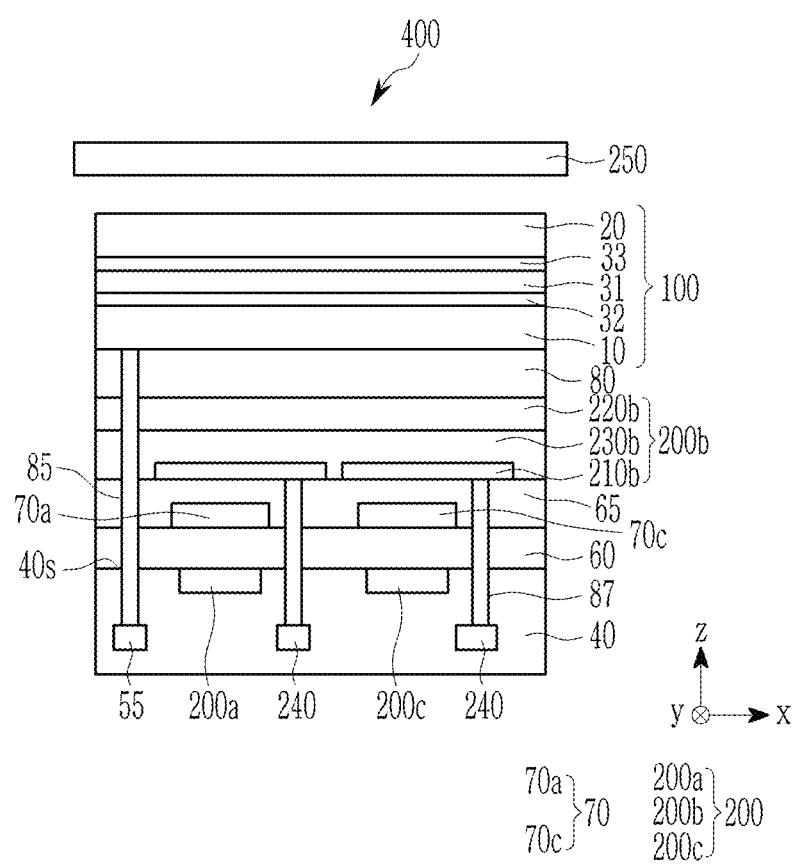
FIG. 5 is a cross-sectional view showing another example of a combination sensor according to some example embodiments.

FIG. 5 is a cross-sectional view showing another example of a combination sensor according to some example embodiments.

The combination sensor 400 according to some example embodiments includes a semiconductor substrate 40, a color filter layer 70, an infrared sensor 100, a visible light sensor 200, and an optical filter 250, as in some example embodiments, including the example embodiments shown in FIG. 4.

The infrared sensor 100 includes a first electrode 10, a second electrode 20, an infrared photoelectric conversion layer 31, and optionally auxiliary layers 32 and 33, and details thereof are the same as described above.

The visible light sensor 200 may be a combination of a photodiode integrated on the semiconductor substrate 40 and a visible light photoelectric conversion device disposed on the semiconductor substrate 40.

In the semiconductor substrate 40, a blue sensor 200a, a red sensor 200c, charge storages 55 and 240, and a transfer transistor (not shown) are integrated. The blue sensor 200a and the red sensor 200c are photodiodes and are disposed to be spaced apart (e.g., isolated from direct contact with each other) in the plane direction (e.g., xy direction), also referred to herein as an in-plane direction, of the semiconductor substrate 40. The blue sensor 200a is integrated in the blue pixel and the red sensor 200c is integrated in the red pixel.

A lower insulating layer 60 and a color filter layer 70 are formed on the semiconductor substrate 40. The color filter layer 70 includes a blue filter 70a overlapped with the blue sensor 200a and a red filter 70c overlapped with the red sensor 200c.

An intermediate insulating layer 65 is formed on the color filter layer 70. The lower insulating layer 60 and the intermediate insulating layer 65 may have trenches 85 and 87 exposing the charge storages 55 and 240. The trenches 85 and 87 may be filled with filler materials. At least one of the lower insulating layer 60 or the intermediate insulating layer 65 may be omitted.

A green sensor 200b is formed on the intermediate insulating layer 65. The green sensor 200b may be a visible light photoelectric conversion device and formed on the whole surface of the semiconductor substrate 40. The green sensor 200b includes a lower electrode 210b and an upper electrode 220b facing each other and a green photoelectric conversion layer 230b disposed between the lower electrode 210b and the upper electrode 220b. Either one of the lower electrode 210b or the upper electrode 220b is an anode, and the other one is a cathode.

Both of the lower electrode 210b and the upper electrode 220b may be light-transmitting electrodes. The light-transmitting electrode may be for example made of a transparent conductor such as indium tin oxide (ITO), indium zinc oxide (IZO) or may be a metal thin film formed with a thin thickness of several nanometers to several tens of nanometer thickness or a single layer or multiple layers of metal thin film formed with a thin thickness of several nanometers to tens of nanometer thickness and doped with metal oxide.

The green photoelectric conversion layer 230b may be configured to selectively absorb light in a green wavelength spectrum and allow light from wavelength spectra other than the green wavelength spectrum, that is, the blue wavelength spectrum and the red wavelength spectrum, to pass through. The green photoelectric conversion layer 230b may be formed on the whole surface of the combination sensor 400. As a result, it may be configured to selectively absorb light in a green wavelength spectrum from the whole surface of the combination sensor 400 and increase light areas, thus having high absorption efficiency.

The green photoelectric conversion layer 230b may selectively absorb light in a green wavelength spectrum, form excitons, and separate the excitons into holes and electrons. The separated holes move towards the anode which is one of the lower electrode 210b or the upper electrode 220b, while the separated electrons move toward the cathode which is the other of the lower electrode 210b or the upper electrode 220b, and thus a photoelectric conversion effect may be obtained. The separated electrons and/or holes may be collected in the charge storage 240.

An auxiliary layer (not shown) may be further included between the lower electrode 210b and the green photoelectric conversion layer 230b and/or between the upper electrode 220b and the green photoelectric conversion layer 230b. The auxiliary layer may be a charge auxiliary layer, a light absorption auxiliary layer, or a combination thereof, but is not limited thereto.

Herein, an example structure in which the blue sensor 200a and the red sensor 200c are photodiodes and the green sensor 200b is a photoelectric conversion device is described, but is not limited thereto. The blue sensor 200a and the green sensor 200b may be photodiodes and the red sensor 200c may be a photoelectric conversion device or the green sensor 200b and the red sensor 200c may be photodiodes and the blue sensor 200a may be a photoelectric conversion device. Accordingly, two of the blue sensor 200a, the green sensor 200b, or the red sensor 200c may be integrated in the semiconductor substrate 40, and another of the blue sensor 200a, the green sensor 200b, or the red sensor 200c may be a visible light photoelectric conversion device on the semiconductor substrate 40 and stacked with the infrared sensor 100 in a depth direction (e.g., the z direction) that is perpendicular to an in-plane direction of the infrared sensor 100 (e.g., both the x and y directions) and/or is perpendicular to an upper surface 40s of the semiconductor substrate 40 (e.g., the z direction).

On the green sensor 200b, an upper insulating layer 80 is formed, and on the upper insulating layer 80, the infrared sensor 100 and the optical filter 250 are disposed. The infrared sensor 100 and the optical filter 250 are the same as described above.

In FIG. 5, a structure in which the infrared sensor 100 is disposed on the green sensor 200b, which is one of the visible light photoelectric conversion devices, is illustrated, but is not limited thereto, and the green sensor 200b may be disposed on the infrared sensor 100.

In FIG. 5, the color filter layer 70 and intermediate insulating layer 65 are between a photoelectric conversion device of the visible light sensor 200 (e.g., the green sensor 200b) and photodiodes of the visible light sensor 200 (e.g., the blue and red sensors 200a and 200c). However, example embodiments are not limited thereto. For example, in some example embodiments, the photoelectric conversion device of the visible light sensor 200 (e.g., the green sensor 200b) may be between the color filter layer 70 and photodiodes of the visible light sensor 200 (e.g., the blue and red sensors 200a and 200c) where the color filters of the color filter layer 70 are each configured to selectively transmit a mixture of the wavelength spectra absorbed by the photoelectric conversion device and a photodiode overlapped by the color filter. For example, sensors 200a-200c may be configured to sense separate ones of red-green-blue (RGB) colors, and color filters 70a, 70c may be configured to selectively transmit separate ones of cyan-magenta-yellow CMY colors. For example, when the green sensor 200b is between the color filter layer 70 and the blue and red sensors 200a and 200c, the blue filter 70a, which overlaps the blue sensor 200a in the depth direction, may be replaced with a cyan filter and the red filter 70c, which overlaps the red sensor 200c in the depth direction, is replaced with a yellow filter. The color filter layer 70, alone or together with the intermediate insulating layer 65, may be between the infrared sensor 100 and the photoelectric conversion device (e.g., green sensor 200b) in the depth direction (e.g., in place of the insulating layer 80). The color filter layer 70, alone or together with the intermediate insulating layer 65, may be between the infrared sensor 100 and the optical filter 250 in the depth direction.

The combination sensor 400 according to some example embodiments may include an infrared sensor 100 and a visible light sensor 200 stacked along the depth direction (e.g., z direction) of the semiconductor substrate 40 and the visible light sensor 200 also has a structure in which a photodiode and a visible light photoelectric conversion device are stacked, thereby further reducing an area of the combination sensor and thus implementing miniaturization of the combination sensor.

Figure 6:
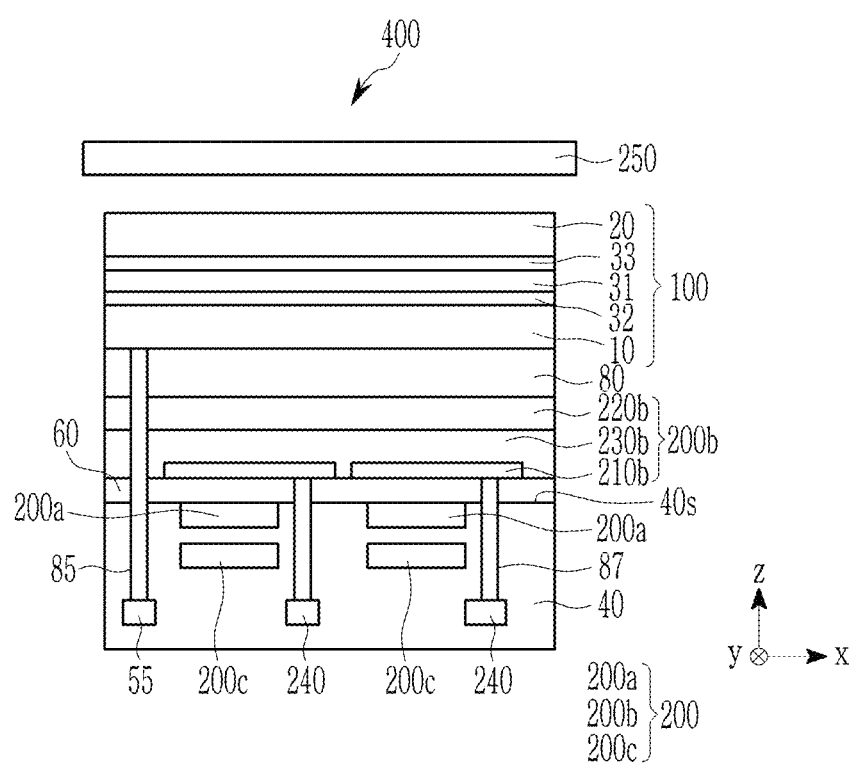
FIG. 6 is a cross-sectional view schematically showing another example of a combination sensor according to some example embodiments.

FIG. 6 is a cross-sectional view schematically showing another example of a combination sensor according to some example embodiments.

Referring to FIG. 6, the combination sensor 400 according to some example embodiments includes a semiconductor substrate 40, an infrared sensor 100, a visible light sensor 200, and an optical filter 250 as in some example embodiments, including the example embodiments shown in at least FIG. 4.

The infrared sensor 100 includes a first electrode 10, a second electrode 20, an infrared photoelectric conversion layer 31, and optionally auxiliary layers 32 and 33, and details are the same as described above.

The visible light sensor 200 include the blue sensor 200a and the red sensor 200c integrated in the semiconductor substrate 40 and a green sensor 200b disposed on the semiconductor substrate 40, wherein the blue sensor 200a and the red sensor 200c may be photodiodes, and the green sensor 200b may be a visible light photoelectric conversion device. The green sensor 200b includes the lower electrode 210b, the green photoelectric conversion layer 230b, and the upper electrode 220b.

However, in the combination sensor 400 according to some example embodiments, the blue sensor 200a and the red sensor 200c integrated in the semiconductor substrate 40 are stacked along a depth direction (e.g., z direction) of the semiconductor substrate 40. The blue sensor 200a and the red sensor 200c may be configured to selectively absorb and sense light in each wavelength spectrum along the stacking depth from the surface 40s of the semiconductor substrate 40. In other words, the red sensor 200c configured to absorb red light in the long wavelength spectrum may be disposed deeper than the blue sensor 200a configured to absorb blue light in the short wavelength spectrum from the surface of the semiconductor substrate 40. In this way, since absorption wavelengths are separated along the stacking depth from the surface 40s of the semiconductor substrate 40, the color filter layer 70 for separating the absorption wavelengths may be omitted.

Herein, the blue sensor 200a and the red sensor 200c are each, for example, illustrated to be photodiodes, while the green sensor 200b is illustrated to be a photoelectric conversion device, but the present inventive concepts are not limited thereto, and the blue sensor 200a and the green sensor 200b may be photodiodes, while the red sensor 200c may be a photoelectric conversion device, or the green sensor 200b and the red sensor 200c may be photodiodes, while the blue sensor 200a may be a photoelectric conversion device.

FIG. 6 exhibits a structure that the infrared sensor 100 is disposed on the green sensor 200b, one of the visible light photoelectric conversion devices, but the present inventive concepts are not limited thereto, and the green sensor 200b may be disposed on the infrared sensor 100.

The combination sensor 400 according to some example embodiments is a combination sensor equipped with the infrared sensor 100 and the visible light sensor 200 which are stacked each other, the visible light sensor 200 is also equipped with a photodiode and a visible light photoelectric conversion device which are stacked each other, and the photodiode also has a stacked structure, resultantly reducing the area of the combination sensor and thus realizing downsizing of the combination sensor. In addition, the combination sensor 400 according to some example embodiments may include no separate color filter layer and thereby may simplify the structure and the process.

Figure 7:
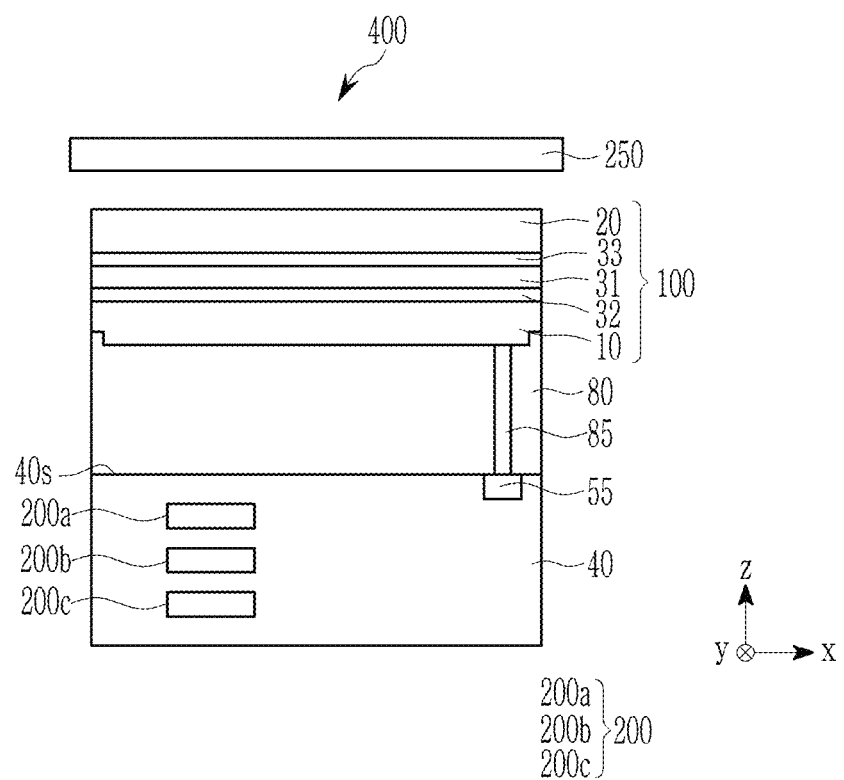
FIG. 7 is a cross-sectional view schematically showing another example of a combination sensor according to some example embodiments.

FIG. 7 is a cross-sectional view schematically showing another example of a combination sensor according to some example embodiments.

Referring to FIG. 7, the combination sensor 400 according to some example embodiments, as in some example embodiments, including the example embodiments shown in at least FIG. 4, includes the semiconductor substrate 40, the infrared sensor 100, the visible light sensor 200, and the optical filter 250.

The infrared sensor 100, as described above, includes the first electrode 10, the second electrode 20, the infrared photoelectric conversion layer 31, and optionally, the auxiliary layers 32 and 33, and details thereof are the same as described above.

The visible light sensor 200 includes the blue sensor 200a, the green sensor 200b, and the red sensor 200c integrated in the semiconductor substrate 40. The blue sensor 200a, the green sensor 200b, and the red sensor 200c are stacked in the semiconductor substrate 40 along the depth direction (e.g., z direction) of the semiconductor substrate 40. The blue sensor 200a, the green sensor 200b, and the red sensor 200c may separate absorption wavelengths along the stacking depth, and accordingly, the color filter layer 70 may be omitted. Between the semiconductor substrate 40 and the infrared sensor 100, the insulating layer 80 may be formed, and the insulating layer 80 has the trench 85. The semiconductor substrate 40 includes the charge storage 55 connected to the infrared sensor 100.

Figure 8:
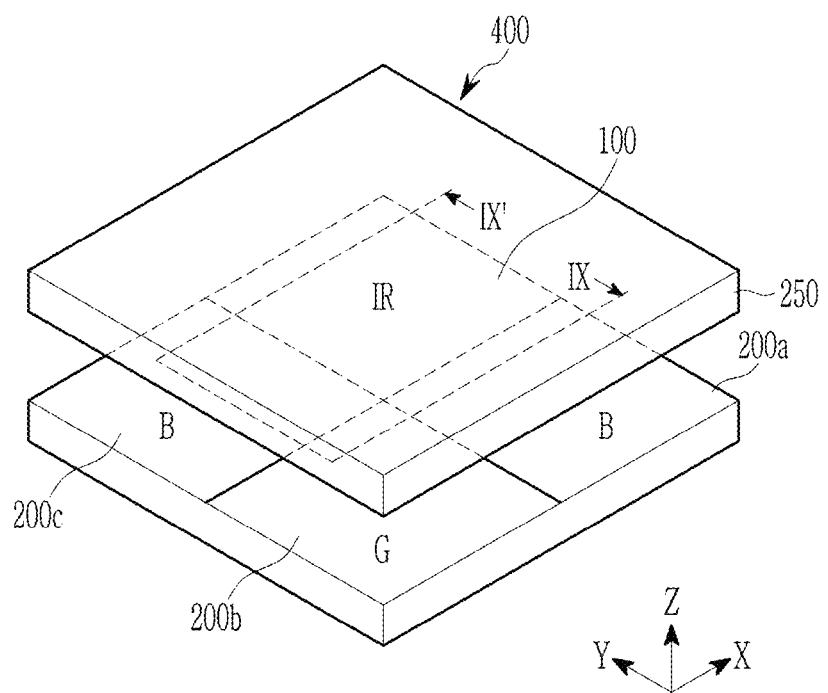
FIG. 8 is a perspective view schematically showing another example of a combination sensor according to some example embodiments.
Figure 9:
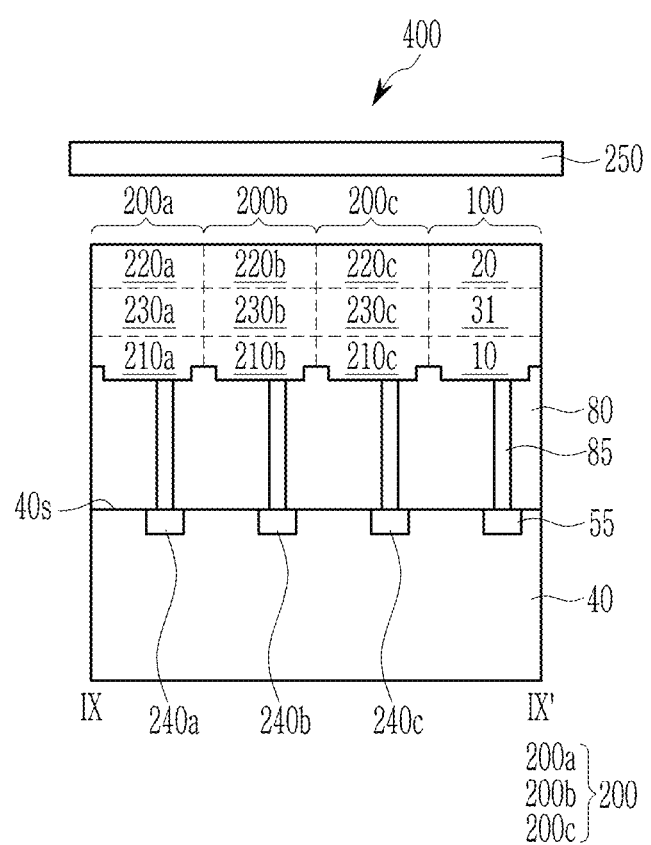
FIG. 9 is a cross-sectional view schematically showing an example of the combination sensor of FIG. 8 along cross-sectional view line IX-IX' of FIG. 8.

FIG. 8 is a perspective view schematically showing another example of a combination sensor according to some example embodiments, and FIG. 9 is a cross-sectional view schematically showing an example of the combination sensor of FIG. 8 along cross-sectional view line IX-IX' of FIG. 8.

Referring to FIGS. 8 and 9, the combination sensor 400 according to some example embodiments, as in some example embodiments, including the example embodiments shown in at least FIG. 4, includes the semiconductor substrate 40; the infrared sensor 100; the visible light sensor 200; the insulating layer 80; and the optical filter 250. The visible light sensor 200 includes the blue sensor 200a, the green sensor 200b, and the red sensor 200c.

The infrared sensor 100, the blue sensor 200a, the green sensor 200b, and the red sensor 200c may be aligned side by side along a plane direction (e.g., xy direction) of the semiconductor substrate 40 and respectively connected, via respective trenches 85, to the charge storages 55, 240a, 240b, 240c integrated in the semiconductor substrate 40.

The blue sensor 200a, the green sensor 200b, and the red sensor 200c may be each visible light photoelectric conversion device.

The infrared sensor 100 includes a first electrode 10, a second electrode 20, an infrared photoelectric conversion layer 31, and optionally auxiliary layers (not shown), and details are the same as described above.

The blue sensor 200a includes a lower electrode 210a, a blue photoelectric conversion layer 230a, and an upper electrode 220a. The green sensor 200b includes a lower electrode 210b, a green photoelectric conversion layer 230b, and an upper electrode 220b. The red sensor 200c includes a lower electrode 210c, a red photoelectric conversion layer 230c, and an upper electrode 220c. The blue photoelectric conversion layer 230a may be configured to absorb light in the blue wavelength spectrum and photoelectrically convert the absorbed light, the green photoelectric conversion layer 230b may be configured to absorb light in the green wavelength spectrum and photoelectrically convert the absorbed light, and the red photoelectric conversion layer 230c may be configured to absorb light in the red wavelength spectrum and photoelectrically convert the absorbed light.

Figure 10:
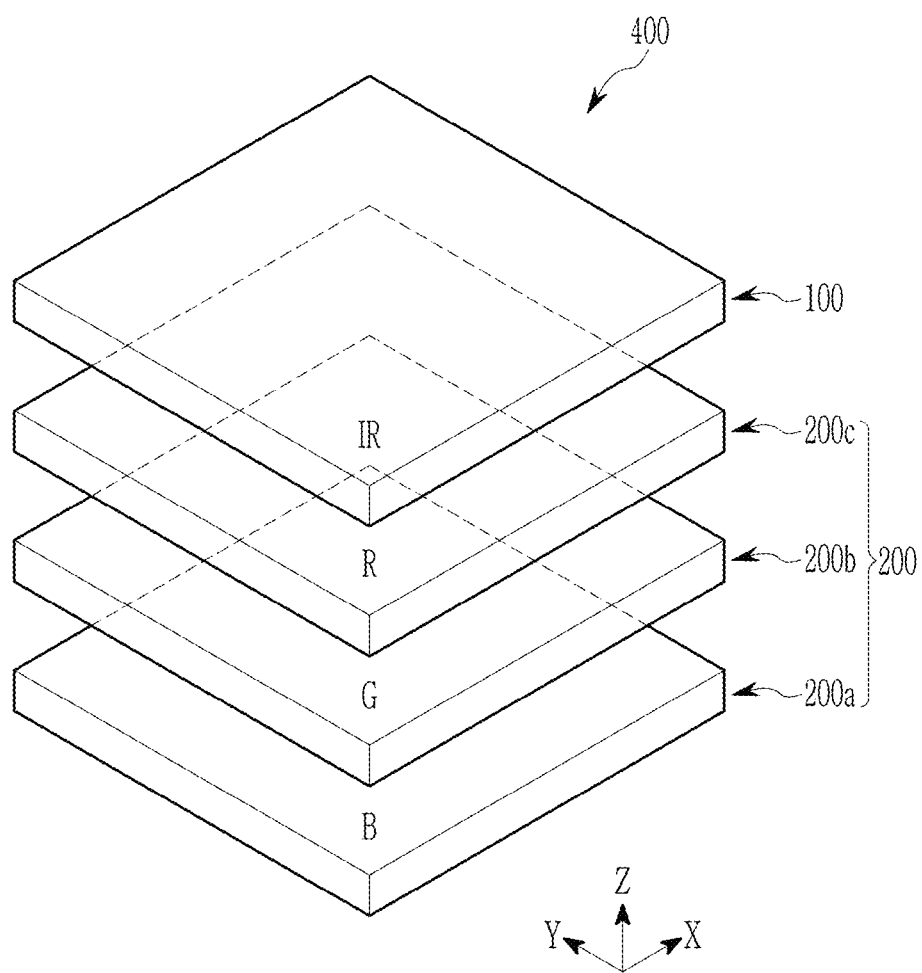
FIG. 10 is a perspective view schematically showing another example of a combination sensor according to some example embodiments.
Figure 11:
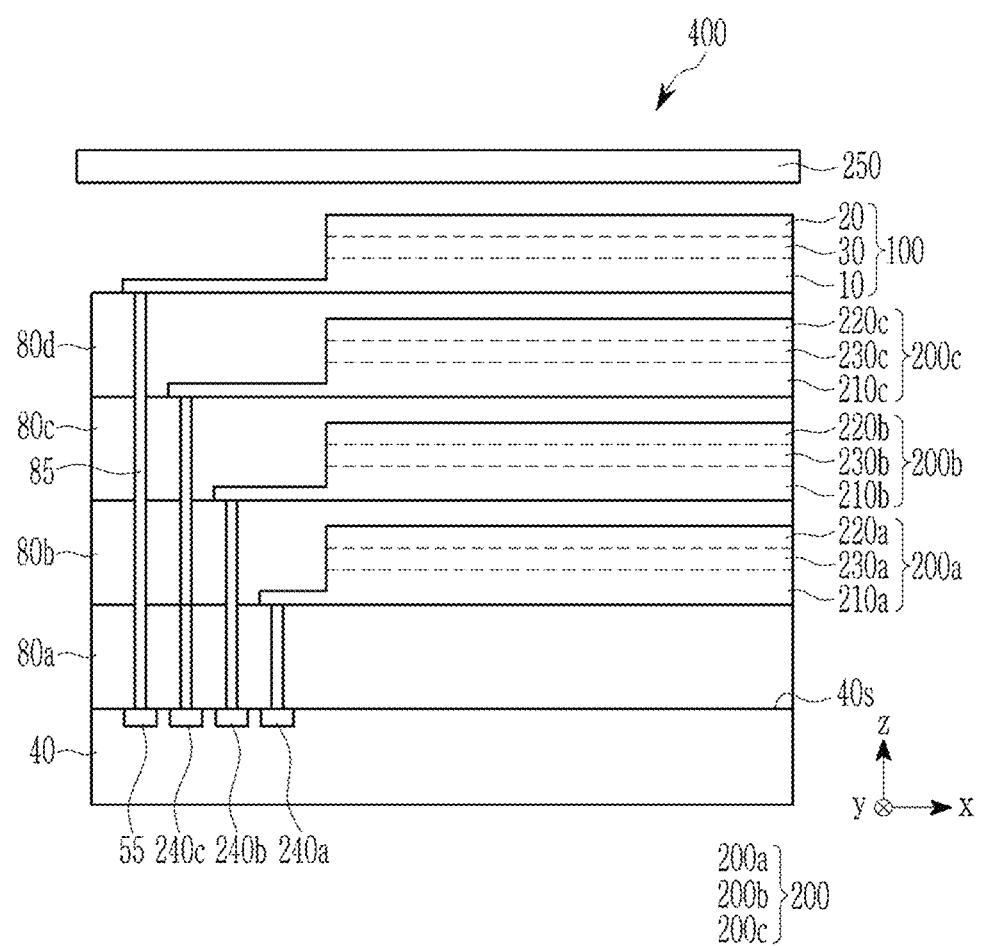
FIG. 11 is a cross-sectional view schematically showing an example of the combination sensor of FIG. 10.

FIG. 10 is a perspective view schematically showing another example of a combination sensor according to some example embodiments, and FIG. 11 is a cross-sectional view schematically showing an example of the combination sensor of FIG. 10.

Referring to FIGS. 10 and 11, the combination sensor 400 according to some example embodiments includes a semiconductor substrate 40; infrared sensor 100; a visible light sensor 200; and an optical filter 250. The visible light sensor 200 includes a blue sensor 200a, a green sensor 200b, and a red sensor 200c.

The infrared sensor 100, the blue sensor 200a, the green sensor 200b, and the red sensor 200c may be stacked along the depth direction (e.g., z direction) of the semiconductor substrate 40 and electrically connected, via respective trenches 85, to each charge storage 55, 240a, 240b, and 240c integrated in the semiconductor substrate 40.

The infrared sensor 100 includes a first electrode 10, a second electrode 20, an infrared photoelectric conversion layer 31, and optionally auxiliary layers (not shown), and details are the same as described above.

The blue sensor 200a includes a lower electrode 210a, a blue photoelectric conversion layer 230a, and an upper electrode 220a. The green sensor 200b includes a lower electrode 210b, a green photoelectric conversion layer 230b, and an upper electrode 220b. The red sensor 200c includes a lower electrode 210c, a red photoelectric conversion layer 230c, and an upper electrode 220c.

Each insulating layer 80a, 80b, 80c, and 80d may be between the semiconductor substrate 40 and the blue sensor 200a, between the blue sensor 200a and the green sensor 200b, between the green sensor 200b and the red sensor 200c, and between the red sensor 200c and the infrared sensor 100.

Some example embodiments illustrate a structure that the infrared sensor 100, the blue sensor 200a, the green sensor 200b, and the red sensor 200c are sequentially stacked but is not limited thereto, and the stacking order may be unlimitedly various. Accordingly, each of the blue sensor 200a, the green sensor 200b, and the red sensor 200c may be a visible light photoelectric conversion device that is stacked with the infrared sensor 100 in a depth direction that is perpendicular to an in-plane direction of the infrared sensor 100 (e.g., both the x and y directions) and/or is perpendicular to an upper surface 40s of the semiconductor substrate 40 (e.g., the z direction).

Referring generally to FIGS. 4-11, a combination sensor 400 may include an infrared sensor 100, a visible light sensor 200, and a semiconductor substrate 40. As shown in at least FIGS. 8-9, the infrared sensor 100 may be arranged in parallel with the visible light sensor 200 along an in-plane direction (e.g., the xy plane) in which both the infrared sensor 100 and the visible light sensor 200 extend. As shown in at least FIGS. 4-7 and FIGS. 10-11, the infrared sensor 100 may be stacked with the visible light sensor along a depth direction of the semiconductor substrate. The depth direction may be understood to be perpendicular to an upper surface 40s of the semiconductor substrate 40. The depth direction may be understood to be perpendicular to the in-plane direction(s) in which the infrared sensor 100 extends, for example the x and y directions.

The aforementioned infrared sensor 100, the CMOS infrared sensor 300, or the combination sensor 400 may be applied to (e.g., included in) various electronic devices, for example, a cell phone, a digital camera, a biometric device, a security device, auto electronic parts, and/or the like, but is not limited thereto.

Figure 12:
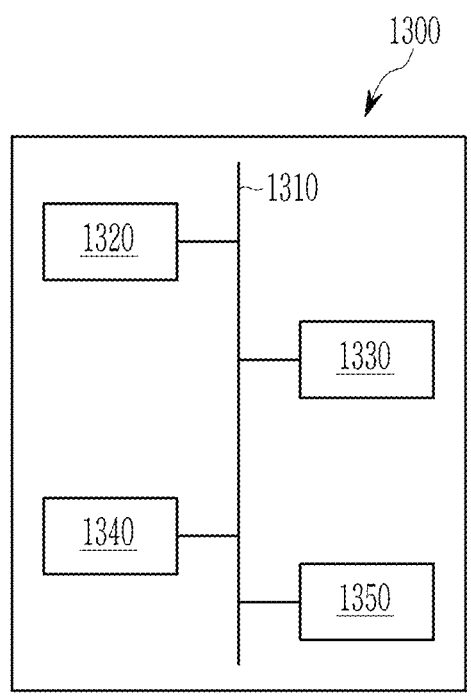
FIG. 12 is a schematic view of an electronic device according to some example embodiments.

FIG. 12 is a schematic view of an electronic device according to some example embodiments.

Referring to FIG. 12, an electronic device 1300 includes a processor 1320, a memory 1330, a sensor 1340, and a display device 1350 (e.g., an OLED display screen device) electrically connected through a bus 1310. The sensor 1340 may be the aforementioned infrared sensor 100, CMOS infrared sensor 300, or combination sensor 400 according to any of the example embodiments and may include the aforementioned film and/or compound. The processor 1320 may perform a memory program and thus at least one function. The processor 1320 may additionally perform a memory program and thus display an image on the display device 1350. The processor 1320 may generate an output.

The processor 1320 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc. The processor 1320 may be configured to generate an output (e.g., an image to be displayed on a display interface) based on such processing.

One or more of the processor 1320, memory 1330, sensor 1340, or display device 1350 may be included in, include, and/or implement one or more instances of processing circuitry such as hardware including logic circuits, a hardware/software combination such as a processor executing software; or a combination thereof. In some example embodiments, said one or more instances of processing circuitry may include, but are not limited to, a central processing unit (CPU), an application processor (AP), an arithmetic logic unit (ALU), a graphic processing unit (GPU), a digital signal processor, a microcomputer, a field programmable gate array (FPGA), a System-on-Chip (SoC) a programmable logic unit, a microprocessor, or an application-specific integrated circuit (ASIC), etc. In some example embodiments, any of the memories, memory units, or the like as described herein may include a non-transitory computer readable storage device, for example a solid state drive (SSD), storing a program of instructions, and the one or more instances of processing circuitry may be configured to execute the program of instructions to implement the functionality of some or all of any of the electronic device 1300, processor 1320, memory 1330, sensor 1340, display device 1350, or the like according to any of the example embodiments as described herein.

Hereinafter, some example embodiments are illustrated in more detail with reference to examples. However, and the scope of the inventive concepts is not limited to these examples.

Synthesis of Compounds

Synthesis Example 1

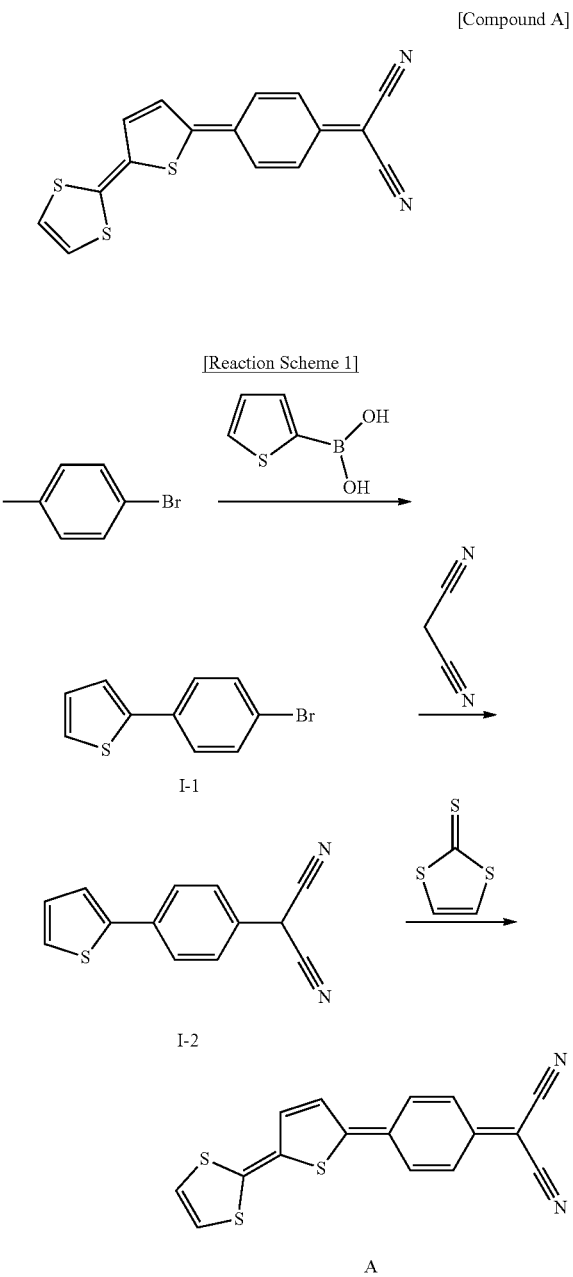

(1) Synthesis of Compound I-1

1-bromo-4-iodobenzene (33.8 g, 120 mmol), 2-thiopheneboronic acid (15.3 g, 120 mmol), potassium carbonate (21.5 g, 155 mmol), and tetrakis(triphenylphosphine)palladium (0) (1 mol %) are dissolved in 150 mL of 1,4-dioxane and 40 mL of $H_2O$ and then, stirred at 80° C. for 24 hours. When a reaction is complete, the resultant is extracted with $H_2O$/chloroform and then, separated and purified through silica gel column chromatography (n-Hex only) to obtain 26.2 g of Compound 1-1. The yield is 92%.

NMR (500 MHz, $CD_2Cl_2$): 7.53 (s, 4H), 7.36 (d, 1H), 7.35 (d, 1H), 7.12 (t, 1H).

(2) Synthesis of Compound 1-2

NaH (60% in mineral oil, 4.5 g, 113 mmol) is dispersed in 130 mL of THF at 0° C. and then, stirred, and a solution prepared by dissolving malononitrile (5.6 g, 85 mmol) in 10 mL of THF is slowly added thereto. After 2 hours, tetrakis(triphenylphosphine)palladium (0) (2 mol %), 1,1'-bis(diphenylphosphino)ferrocene (DPPF, 4 mol %), and Compound I-1 (13.5 g, 56 mmol) are sequentially added thereto and then, stirred at 80° C. for 24 hours. When a reaction is complete, the resultant is cooled down to 0° C., and 100 mL of $H_2O$ is slowly added thereto. Subsequently, THF is all evaporated, and 100 mL of 1 N HCl is slowly added thereto to precipitate a material. The obtained product is extracted with $H_2O$/chloroform and separated and purified through silica gel column chromatography (chloroform only) and thus obtain 10.9 g of Compound 1-2. The yield is 86%.

LC-MS: A molecular weight of 225.07 m/z.

(3) Synthesis of Compound A 1,3-dithiole-2-thione (7.2 g, 53 mmol) and dimethyl sulfate (7.4 g, 58 mmol) are dissolved in 100 mL of acetic acid and then, stirred at 90° C. for 2 hours. Subsequently, Compound 1-2 (10.9 g, 49 mmol) is dissolved in a mixed solvent of 100 mL of acetic acid and 50 mL of triethylamine, and this solution is added to the first reactant and then, stirred at 90° C. for 12 hours. When a reaction is complete, the resultant is poured into 500 mL of acetone and then, filtered. A product therefrom is purified through three more reprecipitation in acetone and finally through sublimation to obtain Compound A.

NMR (500 MHz, DMSO-$d_6$): 8.32 (s, 2H), 8.32 (d, 1H), 7.63 (d, 1H), 7.66 (d, 2H), 6.85 (d, 2H).

Synthesis Example 2

[Compound B]

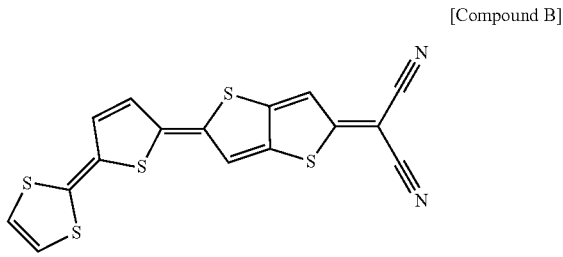

[Reaction Scheme 2]

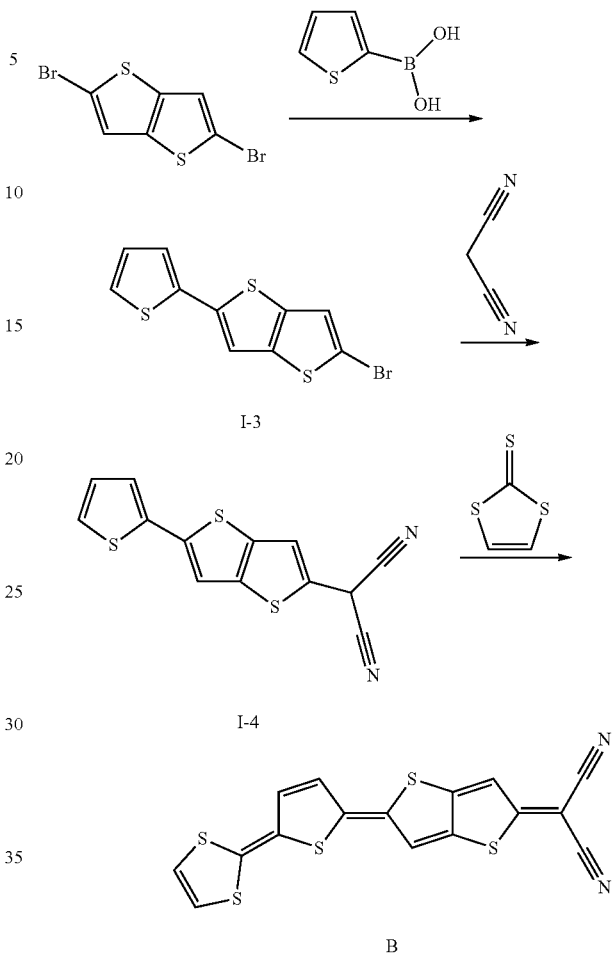

(1) Synthesis of Compound 1-3

2,5-dibromothieno[3,2-b]thiophene (8.9 g, 30 mmol), 2-thiopheneboronic acid (3.8 g, 30 mmol), potassium carbonate (5.3 g, 39 mmol), and tetrakis(triphenylphosphine)palladium (0) (1 mol %) are dissolved in 80 mL of 1,4-dioxane and 20 mL of $H_2O$ and then, stirred at 100° C. for 24 hours. When a reaction is complete, the resultant is extracted with $H_2O$/chloroform and then, separated and purified through silica gel column chromatography (n-Hex only) to obtain 2.6 g of Compound 1-3. The yield is 29%.

LC-MS: A molecular weight of 300.04 m/z.

(2) Synthesis of Compound 1-4

NaH (60% in mineral oil, 0.8 g, 20 mmol) is dispersed in 40 mL of THF at 0° C. and then, stirred, and a solution obtained by dissolving malononitrile (0.9 g, 13 mmol) in 10 mL of THF is slowly added thereto. After 2 hours, tetrakis(triphenylphosphine)palladium (0) (2 mol %), DPPF (4 mol %), and Compound I-3 (2.6 g, 9 mmol) are sequentially added thereto and then, stirred at 80° C. for 24 hours. When a reaction is complete, the resultant is cooled down to 0° C., and 50 mL of $H_2O$ is slowly added thereto. Subsequently, THF is evaporated, and 20 mL of 1N HCl is slowly added thereto to precipitate a material. The obtained product is extracted with H$_2$O/chloroform and then, separated and purified through silica gel column chromatography (chloroform only) to obtain 2.1 g of Compound 1-4. The yield is 85%.

LC-MS: A molecular weight of 287.01 m/z.

(3) Synthesis of Compound B 1,3-dithiole-2-thione (1.0 g, 7.7 mmol) and dimethyl sulfate (1.1 g, 8.4 mmol) are dissolved in 16 mL of acetic acid and then, stirred at 90° C. for 2 hours. Subsequently, Compound 1-4 (2.0 g, 7.0 mmol) is dissolved in a mixed solvent of 16 mL of acetic acid and 8 mL of triethylamine, and this solution is added to the first reactant and then, stirred at 90° C. for 12 hours. When a reaction is complete, 300 mL of acetone is poured thereinto and then, filtered. The obtained product is purified through three more reprecipitation in acetone and finally through sublimation to obtain Compound B.

NMR (500 MHz, DMSO-d$_6$): 8.07 (d, 1H), 8.06 (s, 1H), 7.98 (s, 2H), 7.53 (d, 1H), 6.73 (s, 1H).

Synthesis Example 3

[Compound C]

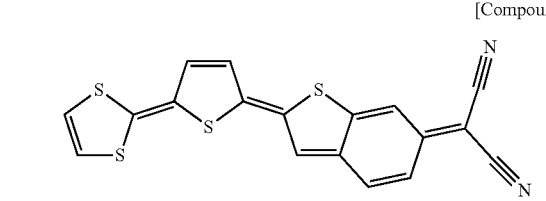

[Reaction Scheme 3]

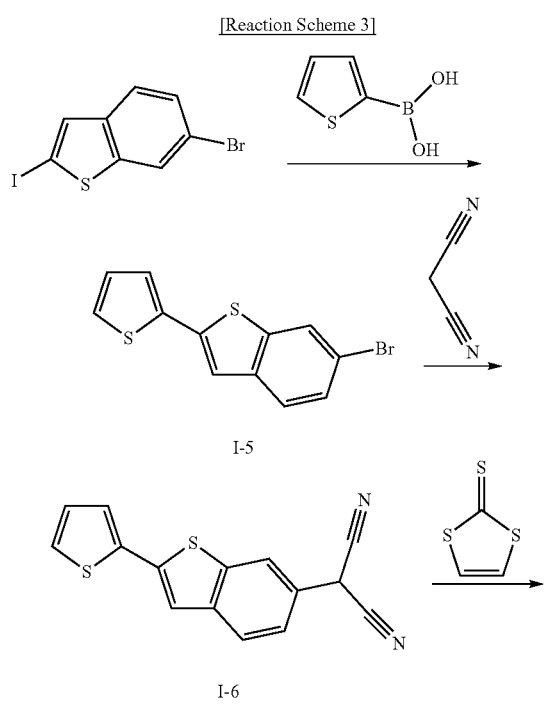

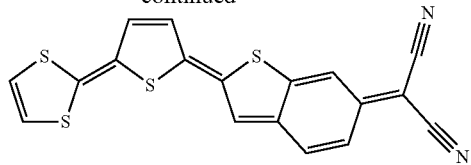

C (1) Synthesis of Compound 1-5

6-bromo-2-iodobenzo[b]thiophene (8.0 g, 23 mmol), 2-thiopheneboronic acid (3.0 g, 23 mmol), potassium carbonate (4.2 g, 30 mmol), and tetrakis(triphenylphosphine)palladium (0) (1 mol %) are dissolved in 80 mL of 1,4-dioxane and 20 mL of H$_2$O and then, stirred at 100° C. for 24 hours. When a reaction is complete, the resultant is extracted with H$_2$O/chloroform and then, separated and purified through silica gel column chromatography (n-Hex only) to obtain 6.1 g of Compound 1-5. The yield is 88%.

NMR (500 MHz, CDCl$_3$): 7.92 (s, 1H), 7.59 (d, 1H), 7.46 (d, 1H), 7.35 (s, 1H), 7.33 (d, 1H), 7.31 (d, 1H), 7.08 (t, 1H).

(2) Synthesis of Compound 1-6

NaH (60% in mineral oil, 2.0 g, 49 mmol) is dispersed in 100 mL of THF at 0° C. and then, stirred, and a solution obtained by dissolving malononitrile (2.3 g, 35 mmol) in 10 mL of THF is slowly added thereto. After 2 hours, tetrakis(triphenylphosphine)palladium (0) (2 mol %), DPPF (4 mol %), and Compound I-5 (6.1 g, 21 mmol) are sequentially added thereto and then, stirred at 80° C. for 24 hours. When a reaction is complete, the resultant is cooled down to 0° C., and 100 mL of H$_2$O is slowly added thereto. Subsequently, THF is evaporated, and 50 mL of 1N HCl is slowly added thereto to precipitate a material. The obtained product is extracted with H$_2$O/chloroform and then, separated and purified through silica gel column chromatography (chloroform alone) to obtain 4.9 g of Compound 1-6. The yield is 85%.

NMR (500 MHz, CDCl$_3$): 7.94 (s, 1H), 7.84 (d, 1H), 7.45 (d, 1H), 7.44 (s, 1H), 7.37 (d, 1H), 7.36 (d, 1H), 7.11 (t, 1H), 5.18 (s, 1H).

(3) Synthesis of Compound C 1,3-dithiole-2-thione (1.0 g, 7.7 mmol) and dimethyl sulfate (1.1 g, 8.4 mmol) are dissolved in 16 mL of acetic acid and then, stirred at 90° C. for 2 hours. Subsequently, Compound 1-6 (2.0 g, 7.1 mmol) is dissolved in a mixed solvent of 16 mL of acetic acid and 8 mL of triethylamine, and this solution is added to the first reactant and then, stirred at 90° C. for 12 hours. When a reaction is complete, the resultant is poured into 300 mL of acetone and then, filtered. The obtained product is purified through three more reprecipitations in acetone and finally through sublimation to obtain Compound C.

MALDI-TOF-MS: A molecular weight of 380.81 m/z.

Synthesis Example 4

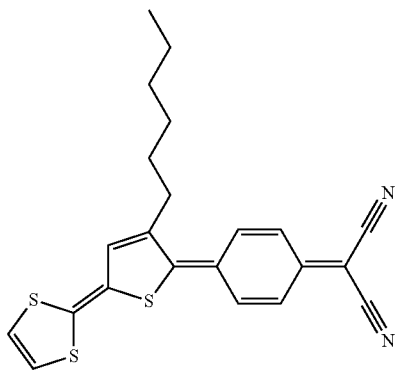
[Compound D]

[Reaction Scheme 4]

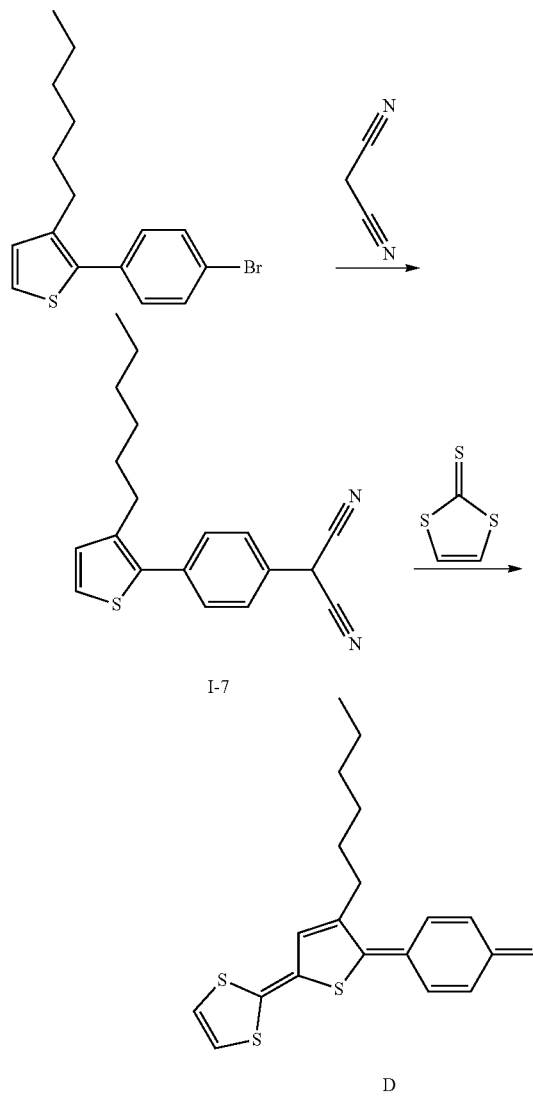

NaH (60% in mineral oil, 2.0 g, 49 mmol) is dispersed in 100 mL of THF at 0° C. and then, stirred, and a solution obtained by dissolving malononitrile (2.3 g, 35 mmol) in 10 mL of THF is slowly added thereto. After 2 hours, tetrakis (triphenylphosphine)palladium (0) (2 mol %), DPPF (4 mol %), and 2-(4-bromophenyl)-3-hexylthiophene (5.5 g, 17 mmol) are sequentially added thereto and then, stirred at 80° C. for 24 hours. When a reaction is complete, the resultant is cooled down to 0° C., and 100 mL of $H_2O$ is slowly added thereto. Subsequently, THF is evaporated, and 50 mL of 1N HCl is slowly added thereto to precipitate a material. The obtained product is extracted with $H_2O$/chloroform and then, separated and purified through silica gel column chromatography (chloroform alone) to obtain 4.7 g of Compound 1-7. The yield is 90%.

NMR (500 MHz, $CDCl_3$): 7.56 (s, 4H), 7.30 (d, 1H), 7.02 (d, 1H), 5.11 (s, 1H), 2.65 (t, 2H), 1.61 (m, 2H), 1.33-1.24 (m, 6H), 0.89 (t, 3H).

(2) Synthesis of Compound D 1,3-dithiole-2-thione (0.24 g, 1.8 mmol) and dimethyl sulfate (0.25 g, 1.9 mmol) are dissolved in 4 mL of acetic acid and then, stirred at 90° C. for 2 hours. Subsequently, Compound 1-7 (0.50 g, 1.6 mmol) is dissolved in a mixed solvent of 4 mL of acetic acid and 2 mL of triethylamine, and this solution is added to the first reactant and then, stirred at 90° C. for 12 hours. When a reaction is complete, the resultant is poured into 100 mL of $H_2O$ and then, filtered. The obtained product is purified through silica gel column chromatography (tetrahydrofuran:chloroform=2:1 v/v) to obtain Compound D.

NMR (500 MHz, $CDCl_3$): 7.37 (s, 2H), 7.34 (s, 1H), 7.30 (d, 2H), 6.99 (d, 2H), 2.75 (t, 2H), 1.69 (m, 2H), 1.45 (t, 2H), 1.37 (m, 4H), 0.93 (t, 3H).

Synthesis Example 5

[Compound E]

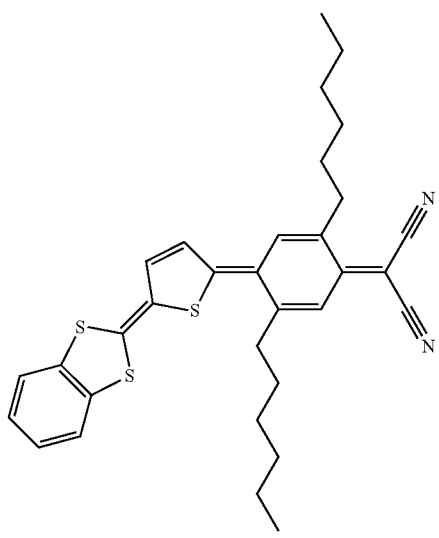

[Reaction Scheme 5]

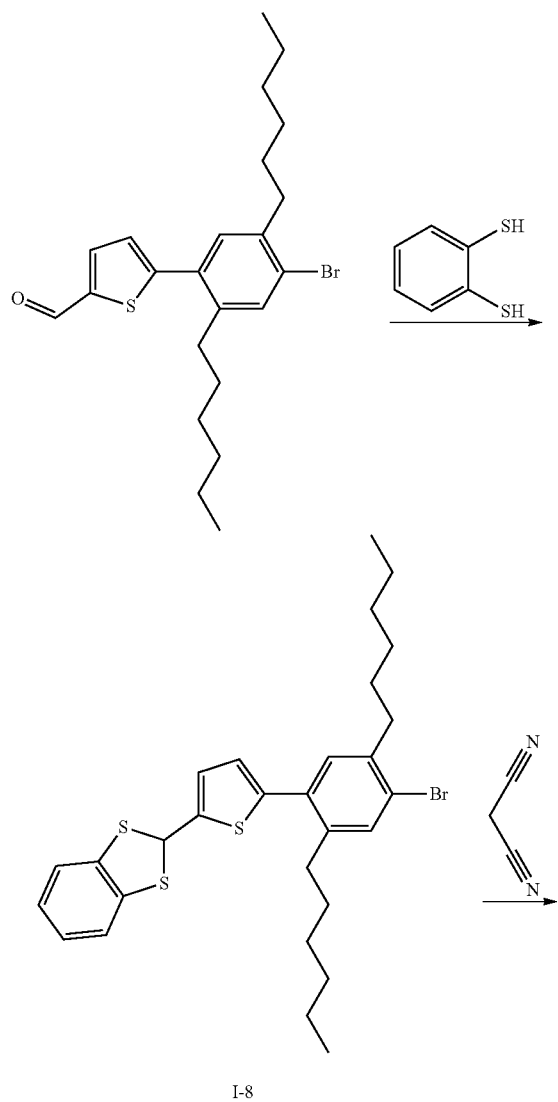

I-8

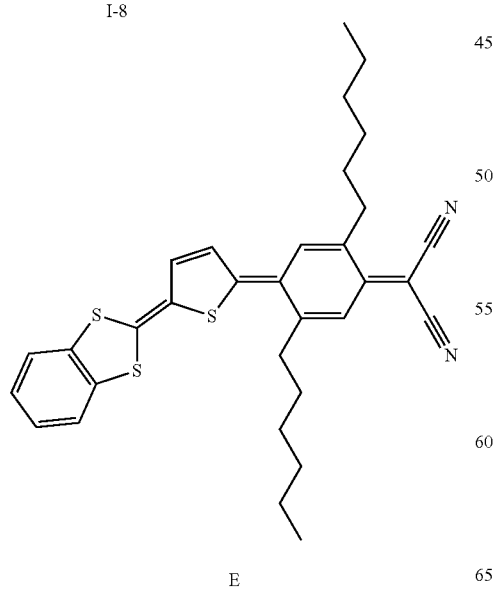

E (1) Synthesis of Compound I-8

5-(4-bromo-2,5-dihexylphenyl)thiophene-2-carbaldehyde (3.1 g, 7.1 mmol), benzene-1,2-dithiol (0.9 g, 6.4 mmol), and p-toluenesulfonic acid monohydrate (0.7 g, 3.6 mmol) are dissolved in 100 mL of toluene and then, stirred at 120° C. for 5 hours. When a reaction is complete, 100 ml of sat. NaHCO$_3$ (aq.) is added, and then the resultant is extracted with H$_2$O/chloroform. The obtained product is purified through silica gel column chromatography (chloroform:n-hexane=1:4 v/v) to obtain 1.9 g of Compound (I-8). The yield is 48%.

LC-MS: A molecular weight of 559.15 m/z.

(2) Synthesis of Compound E

NaH (60% in mineral oil, 0.41 g, 10.2 mmol) is dispersed in 30 mL of THF at 0° C. and then, stirred, and a solution obtained by dissolving malononitrile (0.45 g, 6.8 mmol) in 10 mL of THF is slowly added thereto. After 2 hours, tetrakis(triphenylphosphine)palladium (0) (2 mol %), DPPF (4 mol %), and Compound I-8 (1.9 g, 3.4 mmol) are sequentially added thereto and then, stirred at 80° C. for 24 hours. When a reaction is complete, the resultant is cooled down to 0° C., and 100 mL of H$_2$O is slowly added thereto. Subsequently, THF is evaporated, and 10 mL of 1N HCl is slowly added thereto to precipitate a material. Subsequently, the obtained product is dissolved in 50 ml of chloroform and then saturated solution of p-chloranil is added to the resultant to perform oxidation, and then, separated and purified through silica gel column chromatography (tetrahydrofuranchloroform=1:10 v/v) to obtain Compound E.

NMR (500 MHz, CDCl$_3$): 7.60-7.57 (m, 2H), 7.46 (d, 1H), 7.43-7.41 (m, 2H), 7.38 (d, 1H), 7.26 (s, 1H), 7.10 (s, 1H), 2.86 (t, 2H), 2.81 (t, 2H), 1.63 (m, 4H), 1.50-1.43 (m, 4H), 1.37-1.34 (m, 8H), 0.92 (t, 3H), 0.89 (t, 3H).

Comparative Synthesis Example

[Compound F]

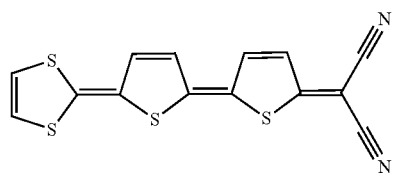

Compound F is synthesized according to a method described in Synthetic Metals 1997, 84 1-3, 395-396.

NMR (500 MHz, DMSO-d$_6$): 7.93 (d, 1H), 7.89 (d, 1H), 7.70 (s, 2H), 7.48 (d, 1H), 6.75 (d, 1H).

Evaluation I

The compounds obtained in the Synthesis Examples and Comparative Synthesis Examples are respectively dissolved in dimethyl sulfoxide (DMSO) at a concentration of 1×10$^{-5}$ M to prepare solutions, and light absorption properties of the compounds in the solutions are evaluated.

The light absorption properties are evaluated by measuring a peak absorption wavelength ($\lambda_{peak,A}$) by using a UV-Vis-NIR spectrometer (UV-3600 Plus, Shimadzu Corp.).

The results are shown in Table 1.

TABLE 1

| | $\lambda_{peak, A1}$ (nm) (solution) |
|---|---|
| Synthesis Example 1 | 776 |
| Synthesis Example 2 | 915 |
| Synthesis Example 3 | 850 |
| Synthesis Example 4 | 753 |
| Synthesis Example 5 | 868 |
| Comparative Synthesis Example | 822 |

Referring to Table 1, the compounds according to the Synthesis Examples and the Comparative Synthesis Example in the solution state exhibit a peak absorption wavelength ($\lambda_{peak,A1}$) in a wavelength spectrum of about 700 nm to about 1000 nm.

Production of Infrared Sensor

Example 1

On a glass substrate, ITO is sputtered to form a 150 nm-thick anode. Subsequently, on the anode, the compound of Synthesis Example 1 and C60 are co-deposited in a volume ratio of 1:1 to form a 150 nm-thick photoelectric conversion layer. On the photoelectric conversion layer, C60 is deposited to form an auxiliary layer. On the auxiliary layer, ITO is sputtered to form a 7 nm-thick cathode. Subsequently, on the cathode, aluminum oxide ($Al_2O_3$) is deposited to form a 50 nm-thick anti-reflection layer and then, sealed with a glass plate to manufacture an infrared sensor.

Example 2

An infrared sensor is manufactured according to the same method as Example 1 except that the compound of Synthesis Example 2 is used instead of the compound of Synthesis Example 1.

Comparative Example

An infrared sensor is manufactured according to the same method as Example 1 except that the compound of Comparative Synthesis Example is used instead of the compound of Synthesis Example 1.

Evaluation II

Peak EQE wavelength ($\lambda_{peak,EQE}$) exhibiting peak external quantum efficiency ($EQE_{peak}$) of the infrared sensors according to the Examples and the Comparative Examples are evaluated.

The external quantum efficiency (EQE) is measured by using an IPCE measurement system (TNE Tech Co., Ltd., Korea). First, the system is calibrated by using an Si photodiode (Hamamatsu Photonics K.K., Japan), and then, the photoelectric conversion devices are mounted thereon to measure the external quantum efficiency (EQE) in a wavelength spectrum of about 400 nm to about 1400 nm and then, the peak EQE wavelength ($\lambda_{peak,EQE}$) showing the peak external quantum efficiency ($EQE_{peak}$).

Figure 13:
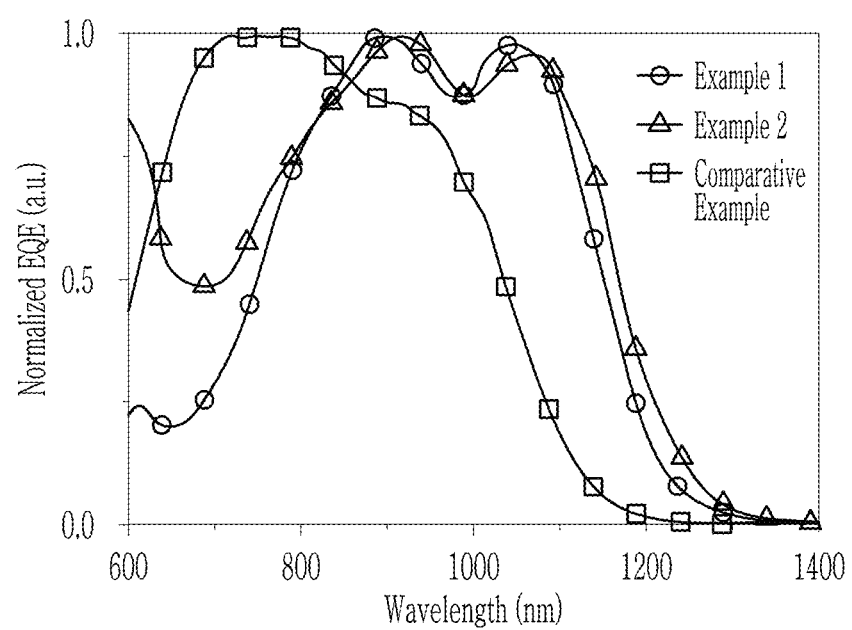
FIG. 13 is a graph showing external quantum efficiency according to wavelengths of infrared sensors according to Examples and Comparative Examples.

The results are shown in Table 2 and FIG. 13.

FIG. 13 is a graph showing external quantum efficiency according to wavelengths of infrared sensors according to the Examples and the Comparative Examples.

TABLE 2

| | $\lambda_{peak, EQE}$ (nm) |
|---|---|
| Example 1 | 900, 1050 |
| Example 2 | 920, 1070 |
| Comparative Example | 720, 910 |

Referring to Table 2 and FIG. 13, when the external quantum efficiency of the infrared sensors is measured to examine light absorption properties of the deposited thin films, the thin films including the compounds of the Synthesis Examples exhibits that a wavelength exhibiting peak external quantum efficiency shifts toward a longer wavelength spectrum, compared with the thin film including the compound of the Comparative Synthesis Example. Herein, a wavelength exhibiting peak external quantum efficiency (e.g., wavelength of incident light at which the infrared sensor exhibits peak external quantum efficiency) corresponds to a peak absorption wavelength of a deposited thin film. As described herein, the infrared sensor may exhibit peak external quantum efficiency ($EQE_{peak}$) at the peak EQE wavelength ($\lambda_{peak,EQE}$) (e.g., the wavelength of incident light that is $\lambda_{peak,EQE}$) of the infrared sensor. As described herein, a peak EQE wavelength ($\lambda_{peak,EQE}$) exhibiting peak external quantum efficiency ($EQE_{peak}$) of an infrared sensor may correspond to a peak absorption wavelength of the infrared sensor. Referring to Tables 1 and 2, the compounds of the Synthesis Examples exhibit much improved molecular alignment and crystallinity, when deposited, and an absorption wavelength spectrum shifted toward a longer wavelength spectrum, compared with the compound of the Comparative Synthesis Example. As shown in Table 2 and FIG. 13, an infrared sensor including the compound may exhibit peak external quantum efficiency ($EQE_{peak}$) at a peak EQE wavelength ($\lambda_{peak,EQE}$) that is between about 1000 nm and about 3000 nm (e.g., about 1000 nm and about 2000 nm, about 1050 nm and about 1070 nm, etc.).

While this disclosure has been described in connection with what is presently considered to be practical example embodiments, it is to be understood that the inventive concepts are not limited to the described example embodiments, but, on the contrary, are intended to cover various modifications and equivalent arrangements included within the spirit and scope of the appended claims.

What is claimed is:

1. A compound represented by Chemical Formula 1:

[Chemical Formula 1]

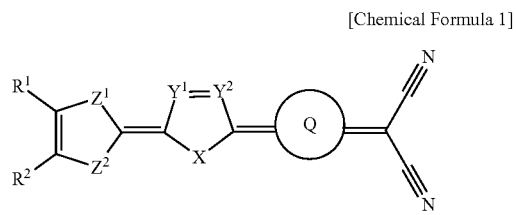

wherein, in Chemical Formula 1,
X is O, S, Se, Te, SO, $So_2$, $NR^a$, $CR^bR^c$, or $SiR^dR^e$,
$Y^1$ and $Y^2$ are independently $CR^f$ or N,
one of $Z^1$ or $Z^2$ is S and another of $Z^1$ or $Z^2$ is O, S, Se, Te, or $NR^g$,
Q is a substituted or unsubstituted C3 to C30 quinoidal ring, Q being different from adjacent quinoidal ring including X, $Y^1$, and $Y^2$, R[1] and R[2] are independently hydrogen, a substituted or unsubstituted C1 to C30 alkyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a substituted or unsubstituted silyl group, a halogen, or a combination thereof, R$^a$ to R$^g$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof, R[1] and R[2] are independently present or are linked to each other to form a ring, R$^b$ and R$^c$ are independently present or are linked to each other to form a ring, R$^d$ and R$^e$ are independently present or are linked to each other to form a ring, and adjacent R$^f$'s are independently present or are linked to each other to form a ring.

2. The compound of claim 1, wherein Q of Chemical Formula 1 includes at least one substituted or unsubstituted 5-membered quinoidal ring, at least one substituted or unsubstituted 6-membered quinoidal ring, or a fused ring thereof.

3. The compound of claim 1, wherein Q of Chemical Formula 1 is one of the groups listed in Group 1:

[Group 1]

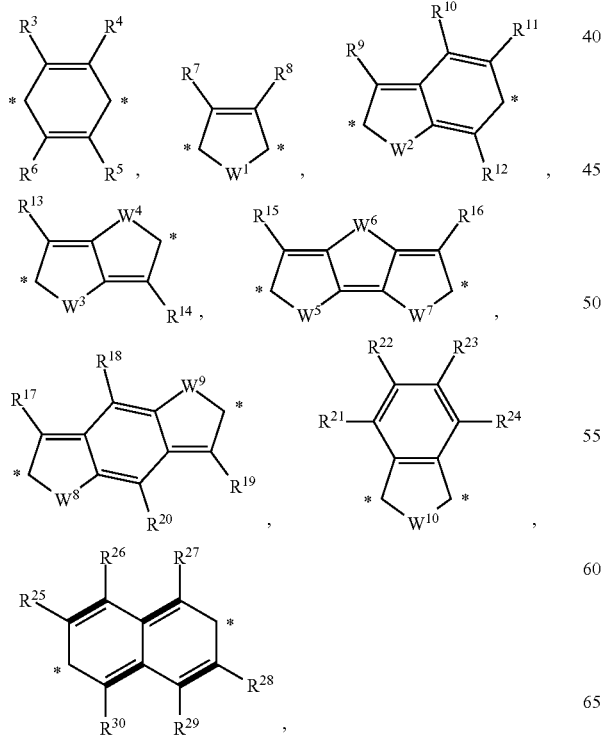

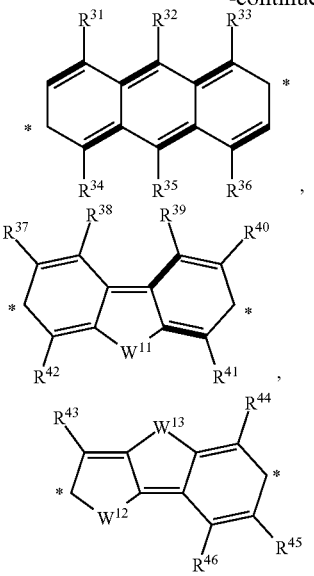

wherein, in Group 1,
W[1] is different from X and is S, Se, or Te,
W[2] to W[13] are independently S, Se or Te,
R[3] to R[46] are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof,
R[3] to R[46] are independently present, or adjacent two of R[3] to R[46] are linked to each other to provide a ring, and
* is a linking point with Chemical Formula 1.

4. The compound of claim 1, wherein X, Z[1], and Z[2] of Chemical Formula 1 are each S.

5. The compound of claim 1, wherein the compound is represented by one of Chemical Formulas 1A to 1I:

[Chemical Formula 1A]

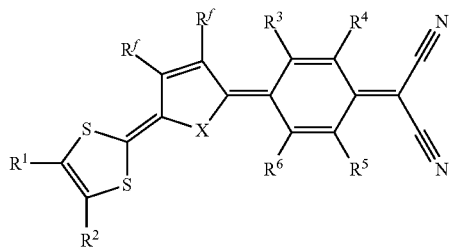

[Chemical Formula 1B]

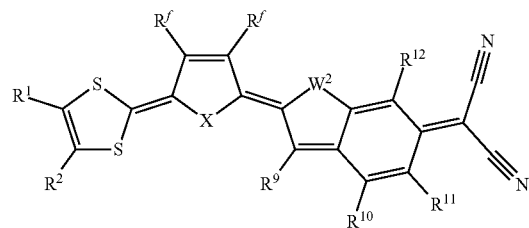

-continued

[Chemical Formula 1C]
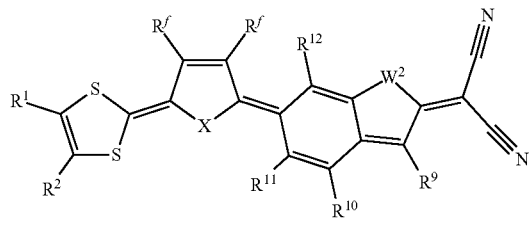

[Chemical Formula 1D]
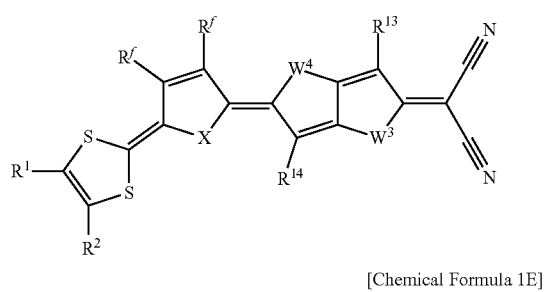

[Chemical Formula 1E]
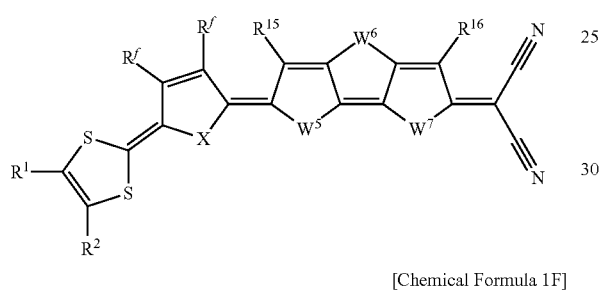

[Chemical Formula 1F]
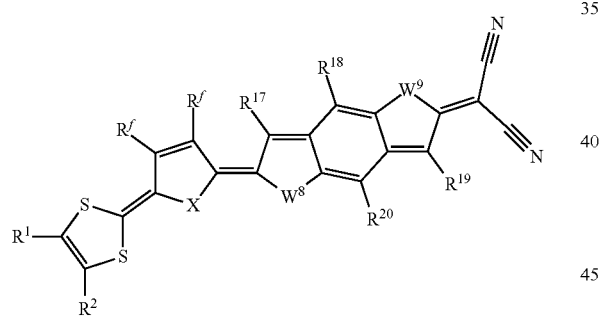

[Chemical Formula 1G]
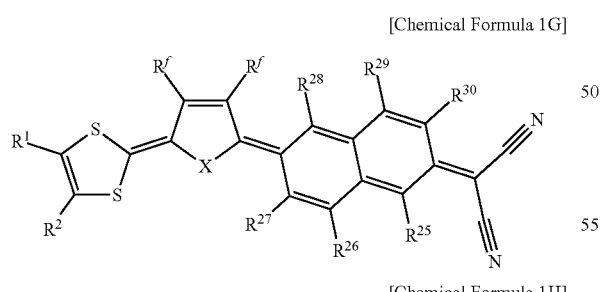

[Chemical Formula 1H]
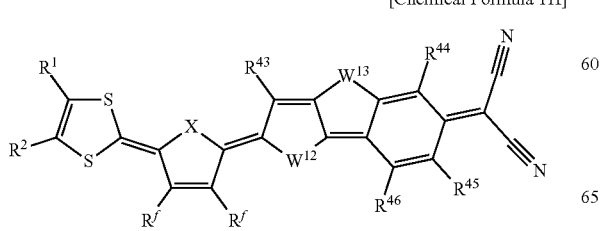

-continued

[Chemical Formula 1I]
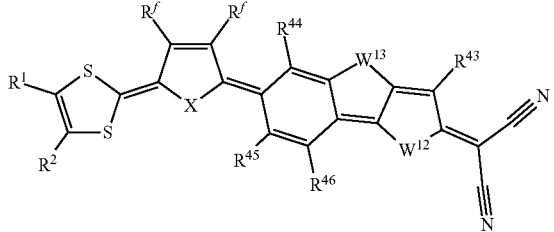

wherein, in Chemical Formulas 1A to 1I,

X is O, S, Se, Te, SO, $SO_2$, $NR^a$, $CR^bR^c$, or $SiR^dR^e$, where $R^a$ to $R^e$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof, $W^2$ to $W^9$, $W^{12}$, and $W^{13}$ are independently S, Se or Te, $R^1$ and $R^2$ are independently hydrogen, a substituted or unsubstituted C1 to C30 alkyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a substituted or unsubstituted silyl group, a halogen, or a combination thereof, and $R^3$ to $R^6$, $R^9$ to $R^{20}$, $R^{25}$ to $R^{30}$, $R^{43}$ to $R^{46}$, and $R^f$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof.

6. The compound of claim 1, wherein the compound is represented by one of Chemical Formulas 1A-1 to 1I-1:

[Chemical Formula 1A-1]
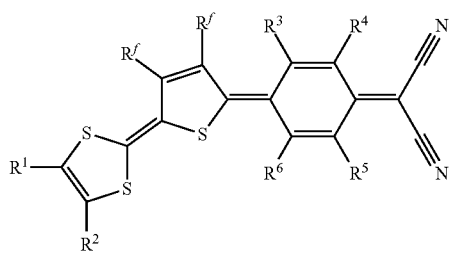

[Chemical Formula 1B-1]
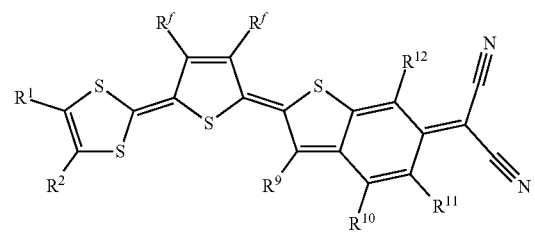

-continued

[Chemical Formula 1C-1]

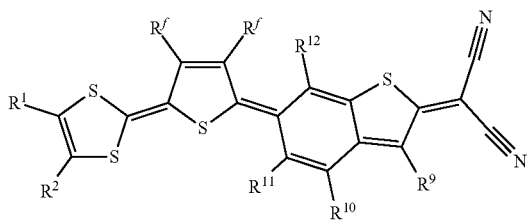

[Chemical Formula 1D-1]

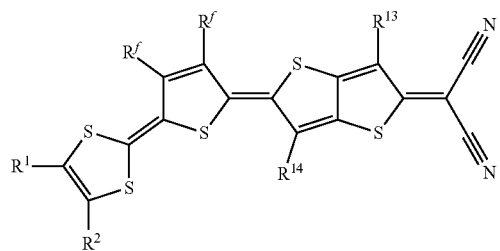

[Chemical Formula 1E-1]

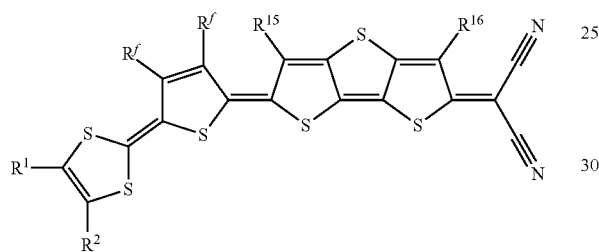

[Chemical Formula 1F-1]

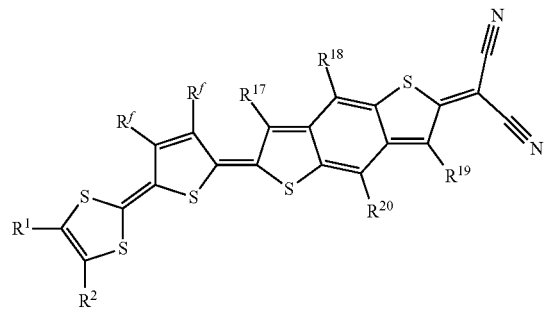

[Chemical Formula 1G-1]

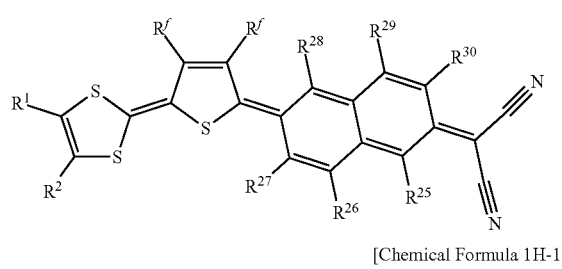

[Chemical Formula 1H-1]

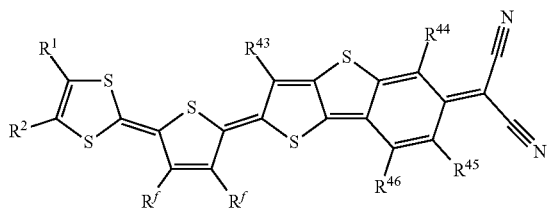

-continued

[Chemical Formula 1I-1]

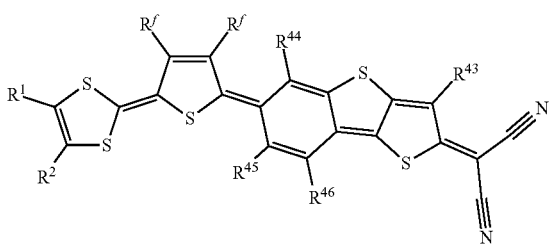

wherein, in Chemical Formulas 1A-1 to 1I-1, $R^1$ and $R^2$ are independently hydrogen, a substituted or unsubstituted C11 to C30 alkyl group, a substituted or unsubstituted C11 to C30 alkoxy group, a substituted or unsubstituted C1 to C30 alkylthio group, a substituted or unsubstituted C6 to C30 aryl group, a substituted or unsubstituted C3 to C30 heterocyclic group, a substituted or unsubstituted silyl group, a halogen, or a combination thereof, and $R^3$ to $R^6$, $R^9$ to $R^{20}$, $R^{25}$ to $R^{30}$, $R^{43}$ to $R^{46}$, and $R^f$ are independently hydrogen, a substituted or unsubstituted C1 to C30 alkyl group, a substituted or unsubstituted C11 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof.

7. A film comprising the compound of claim 1.

8. The film of claim 7, wherein the film has a peak absorption wavelength in a wavelength spectrum of 800 nm to about 3000 nm.

9. An electronic device comprising the film of claim 7.

10. An infrared sensor, comprising:
a first electrode and a second electrode facing each other, and
an organic layer between the first electrode and the second electrode, the organic layer including the compound of claim 1 that is represented by Chemical Formula 1.

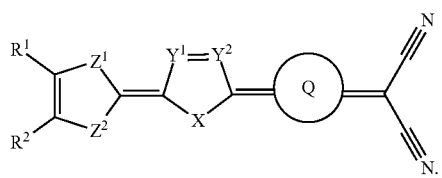

11. The infrared sensor of claim 10, wherein Q of Chemical Formula 1 includes at least one substituted or unsubstituted 5-membered quinoidal ring, at least one substituted or unsubstituted 6-membered quinoidal ring, or a fused ring thereof.

12. The infrared sensor of claim 10, wherein Q in Chemical Formula 1 is one of the groups listed in Group 1:

[Group 1]

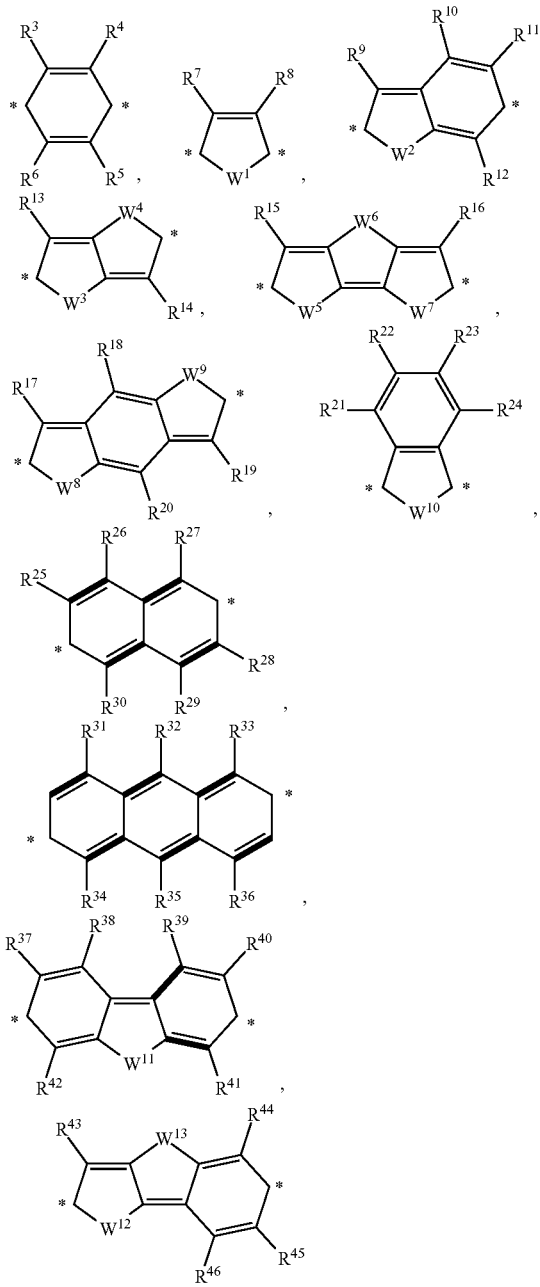

wherein, in Group 1,
  $W^1$ is different from X and is S, Se, or Te,
  $W^2$ to $W^{13}$ are independently S, Se, or Te,
  $R^3$ to $R^{46}$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof,
  $R^3$ to $R^{46}$ are independently present or adjacent two of $R^3$ to $R^{46}$ are linked to each other to provide a ring, and
  * is a linking point with Chemical Formula 1.

13. The infrared sensor of claim 10, wherein the compound is represented by one of Chemical Formulas 1A to 1I:

[Chemical Formula 1A]

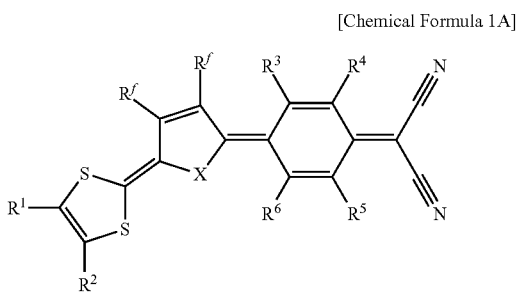

[Chemical Formula 1B]

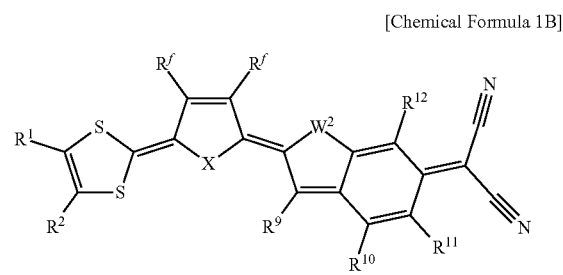

[Chemical Formula 1C]

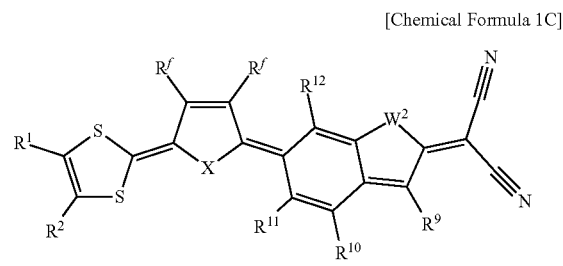

[Chemical Formula 1D]

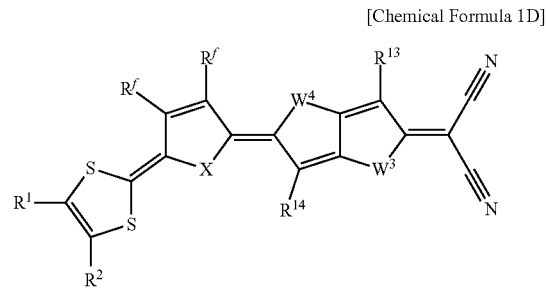

[Chemical Formula 1E]

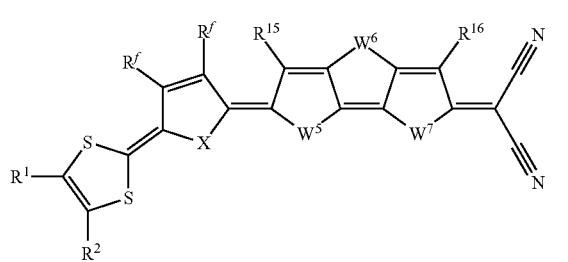

[Chemical Formula 1F]

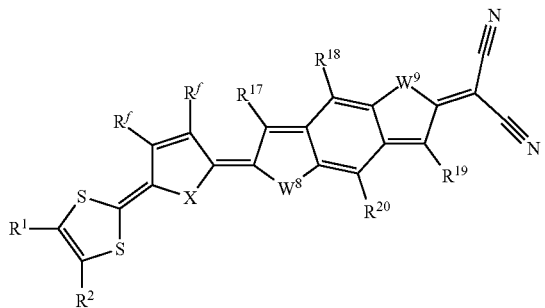

[Chemical Formula 1G]

[Chemical Formula 1H]

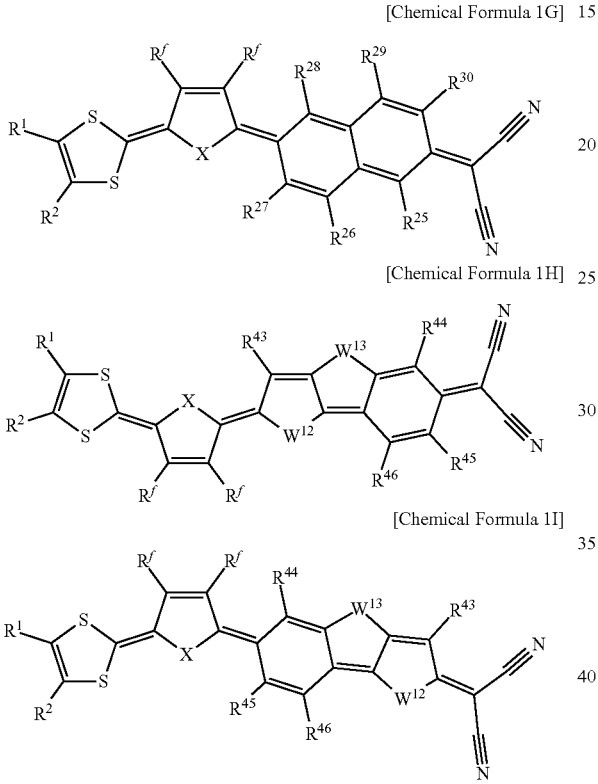

[Chemical Formula 1I]

wherein, in Chemical Formulas 1A to 1I,

X is O, S, Se, Te, SO, So$_2$, NR$^a$, CR$^b$R$^c$, or SiR$^d$R$^e$, where R$^a$ to R$^e$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof, W$^2$ to W$^9$, W$^{12}$, and W$^{13}$ are independently S, Se, or Te, R$^1$ and R$^2$ are independently hydrogen, a substituted or unsubstituted C1 to C30 alkyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a substituted or unsubstituted silyl group, a halogen, or a combination thereof, and R$^3$ to R$^6$, R$^9$ to R$^{20}$, R$^{25}$ to R$^{30}$, R$^{43}$ to R$^{46}$, and R$^f$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof.

14. The infrared sensor of claim 10, wherein the compound is represented by one of Chemical Formulas 1A-1 to 1I-1:

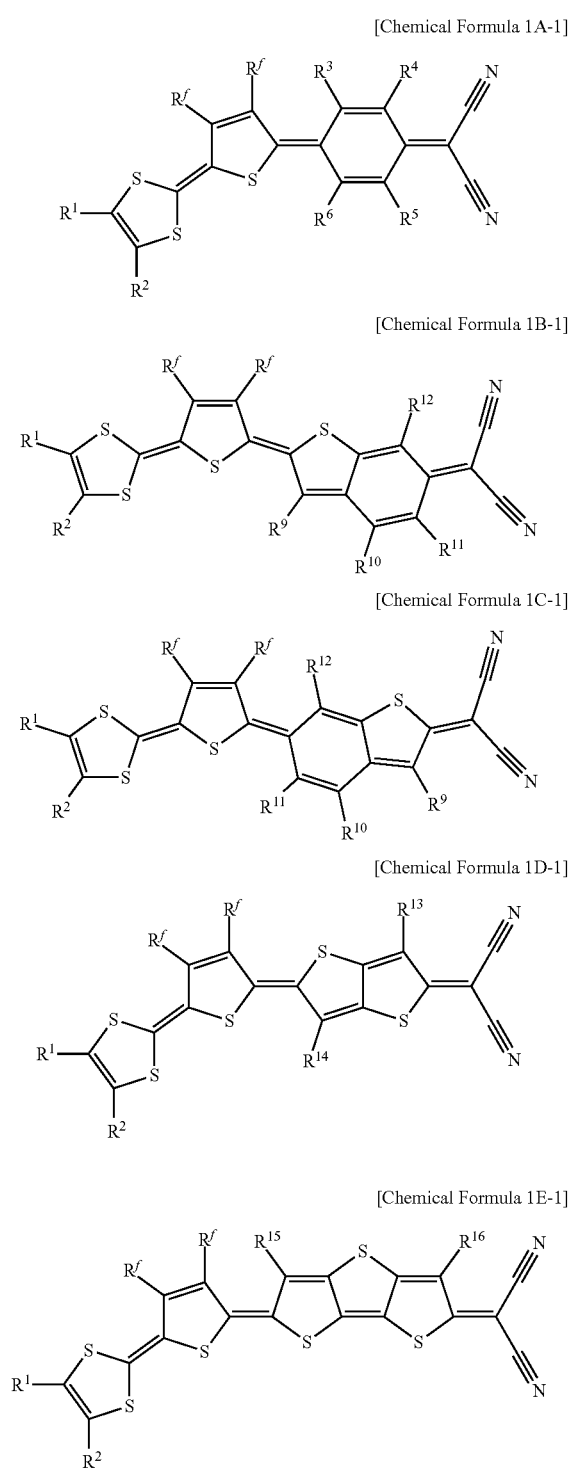

-continued

[Chemical Formula 1F-1]

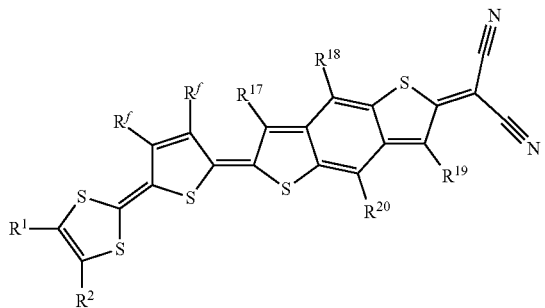

[Chemical Formula 1G-1]

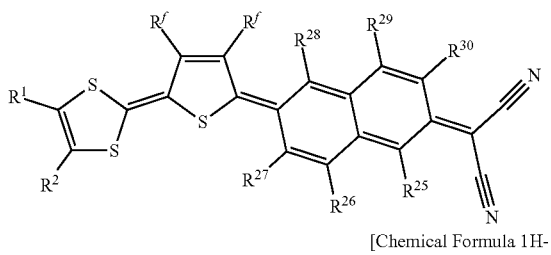

[Chemical Formula 1H-1]

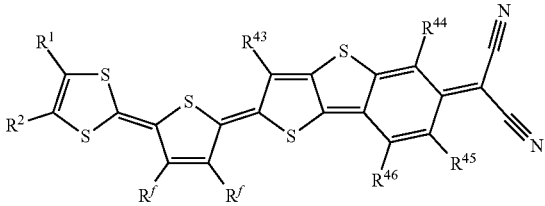

[Chemical Formula 1I-1]

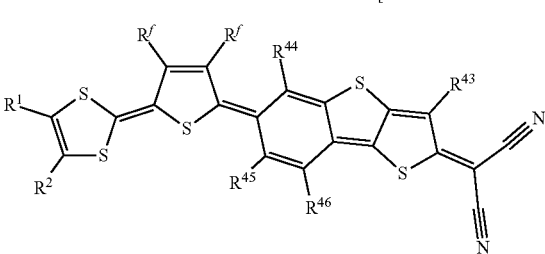

wherein, in Chemical Formulas 1A-1 to 1I-1,
$R^1$ and $R^2$ are independently hydrogen, a substituted or unsubstituted C1 to C30 alkyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a substituted or unsubstituted silyl group, a halogen, or a combination thereof, and
$R^3$ to $R^6$, $R^9$ to $R^{20}$, $R^{25}$ to $R^{30}$, $R^{43}$ to $R^{46}$, and $R^f$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted silyl group, a halogen, a cyano group, or a combination thereof.

15. The infrared sensor of claim 10, wherein the infrared sensor exhibits a peak external quantum efficiency (EQE) with regard to incident light at a peak EQE wavelength that belongs to a wavelength range of about 800 nm to about 3000 nm.

16. The infrared sensor of claim 10, wherein the organic layer comprises an infrared photoelectric conversion layer, and the infrared photoelectric conversion layer comprises the compound and a counter material forming a pn junction with the compound.

17. The infrared sensor of claim 10, wherein the organic layer comprises:
an infrared photoelectric conversion layer, and
an auxiliary layer that is at least one of
between the first electrode and the infrared photoelectric conversion layer, or
between the second electrode and the infrared photoelectric conversion layer.

18. The infrared sensor of claim 17, wherein the auxiliary layer comprises the compound.

19. The infrared sensor of claim 17, wherein the infrared photoelectric conversion layer includes the compound, and the auxiliary layer includes ytterbium (Yb), calcium (Ca), potassium (K), barium (Ba), magnesium (Mg), lithium fluoride (LiF), or an alloy thereof.

20. The infrared sensor of claim 10, further comprising a semiconductor substrate.

21. A combination sensor, comprising:
a first infrared sensor which is the infrared sensor of claim 10, and
a second infrared sensor configured to detect incident light in a shorter wavelength spectrum or a longer wavelength spectrum than the first infrared sensor within an infrared wavelength spectrum,
wherein the first infrared sensor and the second infrared sensor are stacked with each other in a depth direction that is perpendicular to an in-plane direction of the first infrared sensor.

22. A combination sensor, comprising:
a first infrared sensor which is the infrared sensor of claim 10, and
a visible light sensor configured to detect at least a portion of incident light in a visible light wavelength spectrum.

23. The combination sensor of claim 22, further comprising:
a semiconductor substrate,
wherein the infrared sensor is
arranged in parallel with the visible light sensor along an in-plane direction of the semiconductor substrate, or
stacked with the visible light sensor along a depth direction of the semiconductor substrate.

24. The combination sensor of claim 22, wherein
the visible light sensor includes a blue sensor configured to sense light in a blue wavelength spectrum, a green sensor configured to sense light in a green wavelength spectrum, and a red sensor configured to sense light in a red wavelength spectrum, and
each of the blue sensor, the green sensor, and the red sensor are a photodiode integrated in a semiconductor substrate.

25. The combination sensor of claim 22, wherein
the visible light sensor includes a blue sensor configured to sense light in a blue wavelength spectrum, a green sensor configured to sense light in a green wavelength spectrum, and a red sensor configured to sense light in a red wavelength spectrum,
two of the blue sensor, the green sensor, or the red sensor are photodiodes integrated in a semiconductor substrate, and
another of the blue sensor, the green sensor, or the red sensor is a visible light photoelectric conversion device on the semiconductor substrate and stacked with the infrared sensor in a depth direction that is perpendicular to an in-plane direction of the infrared sensor.

26. The combination sensor of claim 22, wherein
the visible light sensor includes a blue sensor configured to sense light in a blue wavelength spectrum, a green sensor configured to sense light in a green wavelength spectrum and a red sensor configured to sense light in a red wavelength spectrum,
each of the blue sensor, the green sensor, and the red sensor is a visible light photoelectric conversion device stacked with the infrared sensor.

27. An electronic device comprising the infrared sensor of claim 10.

28. An electronic device comprising the combination sensor of claim 21.

* * * * *